(12) United States Patent
Ratnakar

(10) Patent No.: US 9,629,521 B2
(45) Date of Patent: Apr. 25, 2017

(54) DUAL VIEW ENDOSCOPE

(71) Applicant: Nitesh Ratnakar, Wheeling, WV (US)

(72) Inventor: Nitesh Ratnakar, Wheeling, WV (US)

( * ) Notice: Subject to any disclaimer, the term of this patent is extended or adjusted under 35 U.S.C. 154(b) by 107 days.

(21) Appl. No.: 14/049,148

(22) Filed: Oct. 8, 2013

(65) Prior Publication Data
US 2014/0107418 A1 Apr. 17, 2014

Related U.S. Application Data

(63) Continuation of application No. 10/711,859, filed on Oct. 11, 2004, now Pat. No. 8,585,584.

(51) Int. Cl.
| | |
|---|---|
| *A61B 1/015* | (2006.01) |
| *A61B 1/05* | (2006.01) |
| *A61B 1/31* | (2006.01) |
| *A61B 1/00* | (2006.01) |
| *A61B 1/005* | (2006.01) |
| *A61B 1/012* | (2006.01) |
| *A61B 1/12* | (2006.01) |

(Continued)

(52) U.S. Cl.
CPC ........ *A61B 1/00181* (2013.01); *A61B 1/0051* (2013.01); *A61B 1/00105* (2013.01); *A61B 1/00179* (2013.01); *A61B 1/015* (2013.01); *A61B 1/018* (2013.01); *A61B 1/0125* (2013.01); *A61B 1/0623* (2013.01); *A61B 1/0676* (2013.01); *A61B 1/12* (2013.01); *A61B 1/126* (2013.01); *A61B 1/00174* (2013.01)

(58) Field of Classification Search
CPC ............ A61B 1/00181; A61B 1/00174; A61B 1/00179; A61B 1/0125; A61B 1/015; A61B 1/018; A61B 1/31; A61B 1/012

USPC .......................................... 600/104, 157, 129
See application file for complete search history.

(56) References Cited

U.S. PATENT DOCUMENTS 3,593,706 A * 7/1971 Schubert ....................... 600/179
3,889,662 A 6/1975 Mitsui
(Continued)

OTHER PUBLICATIONS

Tajiri et al., "Clinical application of an ultra-thin pancreatoscope using a sequential video converter", 39 Gastrointest Endosc. 371 (1993).
(Continued)

*Primary Examiner* — John P Leubecker
(74) *Attorney, Agent, or Firm* — Jundong Ma

(57) ABSTRACT

An endoscope is provided to examine internal organs with front and rear views. The endoscope comprises a shaft extending from a distal end in a rearward direction along a longitudinal axis towards a proximal end, with the distal and proximal ends defining a hollow channel extended therethrough. The endoscope further comprises a first lens positioned adjacent to the distal end and configured to receive a first image in a forward direction along the longitudinal axis, with the forward direction generally 180 degree from the rearward direction. The endoscope further comprises a rearview module positioned adjacent to the distal end. The rearview module comprises a second lens configured to be positioned adjacent to the distal end, and receive a second image in a target direction having a directional component in the rearward direction along the longitudinal axis, independently of the first lens receiving the first image in the forward direction.

10 Claims, 31 Drawing Sheets

(51) Int. Cl.
  *A61B 1/06*   (2006.01)
  *A61B 1/018*  (2006.01)

(56) References Cited

U.S. PATENT DOCUMENTS

| | | | |
|---|---|---|---|
| 3,903,877 A * | 9/1975 | Terada | 600/157 |
| 3,918,438 A * | 11/1975 | Hayamizu et al. | 600/168 |
| 4,573,450 A * | 3/1986 | Arakawa | 600/104 |
| 4,641,635 A * | 2/1987 | Yabe | 600/130 |
| 4,832,473 A | 5/1989 | Ueda | |
| 4,846,154 A | 7/1989 | MacAnally et al. | |
| 4,982,725 A | 1/1991 | Hibino et al. | |
| 5,166,787 A | 11/1992 | Irion | |
| 5,168,864 A | 12/1992 | Shockey | |
| 5,178,130 A | 1/1993 | Kaiya | |
| 5,209,219 A * | 5/1993 | Hollobaugh | A61M 3/0279 600/108 |
| 5,269,289 A * | 12/1993 | Takehana et al. | 600/109 |
| 5,325,847 A * | 7/1994 | Matsuno | 600/109 |
| 5,427,087 A * | 6/1995 | Ito et al. | 600/109 |
| 5,547,455 A * | 8/1996 | McKenna et al. | 600/113 |
| 5,554,098 A | 9/1996 | Yabe et al. | |
| 5,604,531 A * | 2/1997 | Iddan et al. | 348/76 |
| 5,653,677 A | 8/1997 | Okada et al. | |
| 5,940,126 A | 8/1999 | Kimura | |
| 6,066,090 A | 5/2000 | Yoon | |
| 6,409,657 B1 * | 6/2002 | Kawano | 600/157 |
| 6,468,203 B2 | 10/2002 | Belson | |
| 6,482,149 B1 | 11/2002 | Torii | |
| 6,780,151 B2 | 8/2004 | Grabover et al. | |
| 6,916,286 B2 | 7/2005 | Kazakevich | |
| 6,916,332 B2 * | 7/2005 | Adams | 606/219 |
| 6,997,871 B2 | 2/2006 | Sonnenschein et al. | |
| 7,758,499 B2 * | 7/2010 | Adler | 600/158 |
| 2002/0099267 A1 | 7/2002 | Wendlandt et al. | |
| 2003/0120130 A1 * | 6/2003 | Glukhovsky et al. | 600/109 |
| 2005/0165272 A1 | 7/2005 | Okada et al. | |
| 2007/0032700 A1 | 2/2007 | Fowler et al. | |
| 2007/0142710 A1 | 6/2007 | Yokoi et al. | |

OTHER PUBLICATIONS

Shaker, "Unsedated trans-nasal pharyngoesophagogastroduodenoscopy (T-EGO): technique", 40 Gasrointest Endosc. 346 (1994).

* cited by examiner

DUAL VIEW ENDOSCOPE

CROSS-REFERENCE TO RELATED APPLICATION

This application is a continuation application under 35 U.S.C. §120 of U.S. Non-provisional patent application Ser. No. 10/711,859, filed on Oct. 11, 2004, now issued to patent as U.S. Pat. No. 8,585,584, the entire disclosure of the aforesaid prior application being incorporated herein by reference.

DESCRIPTION

Field of Invention

The present invention relates to endoscopes, more specifically to endoscopes that provide both forward and rear view in a hollow body organ.

Background and Prior Art

Endoscopes are used to perform a variety of surgical procedures. FIGS. 1 and 2 illustrate an embodiment of a conventional endoscope. It has a handle from which extends a flexible shaft, which is inserted into a hollow organ to be inspected. The shaft consists of a proximal section, insertion tube, bending section and a stiff section. The shaft terminates in the distal end, which typically houses image lens, illumination bulb, air/water nozzle and an instrument channel outlet. Light is transmitted from a light source through the shaft via an electric cable to the illumination bulb. The illumination bulb illuminates the area to be examined. The image lens captures images of the illuminated area. The image is then transmitted through a fiber optic cable and viewed through an eyepiece on the handle of the endoscope. Alternatively, the image is converted to a video signal and transmitted to an image processor by an electrical cable. The image is then processed and displayed on a display unit like a computer monitor. The handle of the endoscope has an extension arm that attaches the endoscope to a light source and an image processor.

To enable the endoscope to maneuver through the turns of a hollow organ the shaft is flexible and incorporates a multitude of cables that attach the bending portion with actuators. Tension is applied to these cables to move the bending portion in various directions. This is done by manual adjustment of actuators on the handle of the endoscope. Typically, there are two pairs of such cables passing within the shaft, one pair for flexing the bending portion in one plane and the other pair for flexing it in an orthogonal plane.

It is also usual to provide two channels extending between the handle and the distal end of the shaft, an air/water channel and an instrument channel. The air/water channel is used to insufflate air in a hollow organ to expand it for proper visualization. The air/water channel is connected proximally to an air/water pump (not shown) and to distally to the air/water channel outlet. The image lens and the illumination bulb are frequently smeared with blood, stool or other body fluids while in a hollow organ which obstructs a clear view. In such a situation, the air/water channel is used to eject water or blow air at the image lens and/or illumination bulb in order to clean them while still inside a hollow organ. The instrument channel has an inlet proximally and an outlet distally. It is used to pass various surgical instruments to do various surgical procedures. It is also used to apply suction to remove fluids, air and other materials from within a hollow organ during examination.

Endoscope is typically inserted into the patient either thorough a natural body orifice like anus or mouth or it is inserted through a surgical incision. It is then steered to a desired location by adjusting the bending portion and manually pushing the endoscope. After reaching the desired location, the endoscope is withdrawn. Typically it is during pullout when the inside of a hollow organ like colon is thoroughly examined. Insertion of the endoscope into a hollow organ is a risky maneuver and is associated with significant complications like trauma, bleeding and perforation. It is generally desirable to complete the examination with a single insertion to minimize complications.

The present endoscopes have significant limitations. As shown in FIG. 3 they are only forward viewing. Currently, rear view can only be obtained by bending the distal portion of the endoscope back upon itself in a 'retro flexion' maneuver as shown in FIG. 4B. However, it is not possible to achieve retro flexion in many narrow hollow organs like colon, esophagus, duodenum and small bowel. Also, retro flexion compromises forward view. Hence with conventional endoscopes, only one view, forward or backward, is possible at a given time. The present endoscopes also have a narrow field of vision with an angle of vision of about 120 degrees. A large number of significant pathologic findings are frequently missed during endoscopic examination because the inability to obtain rear view and a narrow field of vision of conventional endoscopes.

This is especially true for colonoscopy where the inside of the colon is examined with an endoscope. Many cancers and pre cancerous lesions (polyps) are frequently missed during colonoscopy (Pickhardt et al, New England Journal of Medicine 2003; 349: 2191-2200). This has serious consequences including death, many of which can easily be prevented. Majority of the missed lesions lie on the rear side of mucosal folds (Pickhardt et al; Annals of Internal Medicine 2004; 141: 352-360). With forward viewing endoscopes, the front of mucosal folds obstructs visualization of the rear side as shown in FIG. 4A. Currently, the rear side of a mucosal fold can only be examined by pushing the tip of the endoscope beyond the fold and bending the endoscope back upon itself in a 'retro flexion' maneuver as shown in FIG. 4B. However, it is frequently not possible to achieve retro flexion in a narrow hollow organ like colon.

Also, retro flexion maneuver compromises the forward view. With conventional endoscopes, only one view, forward or backward, is possible at a given time. Complete examination of colon that includes both forward and rear views currently requires multiple insertions, one to obtain forward view and other to obtain backward view by retro flexion. Both, retro flexion and multiple insertions, independently increase the morbidity, mortality, time and cost of colonoscopy. Moreover, intra colonic retro flexion can not be obtained frequently because of a narrow colonic lumen. Also, conventional endoscopes have a narrow field of vision of about 120 degrees. Some lesions that are missed lie outside of the field of view of conventional endoscopes.

The rear side of the mucosal folds is also hard to access with conventional endoscopes, which have the instrument channel outlet only on the distal end. These areas can only be visualized by retro flexion, which narrows and sometimes obliterates the lumen of the instrument channel. Also, many surgical instruments are not flexible enough to follow the path of a retroflexed endoscope. It is difficult and many times impossible to pass surgical instruments through the instrument channel when the endoscope is retroflexed and surgical procedures can not be performed on the rear side of the mucosal folds.

SUMMARY OF THE INVENTION

In light of the significant limitations discussed above, there is a need for an endoscopic system that provides both forward and rear view and widens the field of vision. It should also enable surgical procedures to be done in areas that are otherwise inaccessible and lie outside of field of vision of the conventional endoscopes. The present invention addresses these unmet needs.

The present invention enables rear view even in organs with a narrow lumen without the need to retro flex the endoscope. This is achieved by strategically adding a suitably designed 'rear view module' to a conventional endoscope. The rear view module consists of a rear image lens and a rear illumination bulb. The rear view module is a solid or tubular structure that can be of different shapes, sizes and configurations as illustrated in the preferred embodiments of the present invention. It is attached to the endoscope in different ways as illustrated in the preferred embodiments of the present invention. Once deployed, the rear view module positions the rear image lens and the rear illumination bulb facing backward. In this position, the rear illumination bulb illuminates the rear area and the rear image lens gives a rear view. The rear image lens is connected to an image processor and the rear illumination bulb is connected to a power source by electrical cables. The rear image lens and the rear illumination bulb can be used simultaneously or separately from the main image lens and the main illumination bulb, as chosen by the operator. Simultaneous forward and rear view can thus be obtained by using the forward image lens and the rear image lens together at a given time. This has the advantage of allowing a thorough examination of a hollow organ that includes both forward and rear views in a single passage.

The present invention has a rear instrument channel and a rear instrument channel outlet. The rear instrument channel is connected to the main instrument channel and the connecting passage has a control valve. Typically deployment of the rear view module automatically opens the passage to the rear instrument channel. Alternatively, the valve can have an independent control. The rear instrument channel is used to pass surgical instruments to do various surgical procedures in areas that would otherwise be inaccessible. It also enables the operator to direct suction in areas under the view of the rear image lens.

The present invention has a rear air/water channel and a rear air/water nozzle located on the shaft of the endoscope. The rear air/water channel is connected to the main air/water channel of the endoscope and the connecting passage has a control valve. Typically, deployment of the rear view module automatically opens the passage to the rear air/water channel. Alternatively, the valve can be controlled independently. The rear air/water channel enables the operator to insufflate air and distend the area under the view of rear image lens. Adequate distension of a hollow organ is essential to obtain a clear and complete view. The rear air/water channel also provides a water jet and a stream of air to clean the rear image lens and rear illumination bulb while inside a hollow body organ.

Additional features and advantages of the present invention will be set forth in the description and drawings which follow or may be learned by practice of the invention.

DESCRIPTION OF THE PREFERRED EMBODIMENTS

Reference will now be made in detail to the preferred embodiments of the invention, examples of which are illustrated in the accompanying drawings. Wherever possible, the same reference numbers will be used throughout the drawings to refer to the same or like parts. The following general description applies to preferred embodiments of the present invention.

The present invention comprises of a rear view module. It is a solid structure that can be rectangular, square, tubular, discoid or of any other shape. It is attached to a conventional endoscope by a suitable mechanical articulation such as ball socket joint, hinge joint, biplanar rolling joint etc. The rear view module consists of a rear image lens to obtain a rear view. The rear image lens is attached to an image processor by an electric cable. This cable transmits the image obtained by the rear image lens to the image processor. After being processed, the image is then viewed on a computer monitor or any other display unit.

The rear view module also contains a rear illumination bulb. The rear illumination bulb is connected to a power source by a cable. The rear illumination bulb uses this light to illuminate the area under view of the rear image lens. The rear image lens and the rear illumination bulb are typically activated upon deployment of the rear view module. The rear view module is deployed using an actuator.

A rear instrument channel is provided in the present invention. It is placed proximal to the rear view module. This channel is connected to the main instrument channel and the passage is controlled by a control valve. Typically, deployment of the rear view module opens the passage to the rear instrument channel. The rear instrument channel is used to pass surgical instruments to do various surgical procedures in areas under view of the rear image lens. It is also used to apply suction in the area under view of the rear image lens.

A rear air/water channel is provided in the present invention. It is placed proximal to the rear view module. The rear air/water channel is connected to the air/water channel of the main endoscope and the passage is controlled by a valve. Typically, deployment of the rear view module opens the passage to the rear air/water channel. The rear air/water channel is used to insufflate air in the direction of view of the rear image lens for better distension and visualization. The air/water channel is also used to squirt water or air at the rear image lens and the rear illumination bulb. This enables cleaning of the rear image lens and the rear illumination bulb while still inside a hollow body organ.

Figure 1:
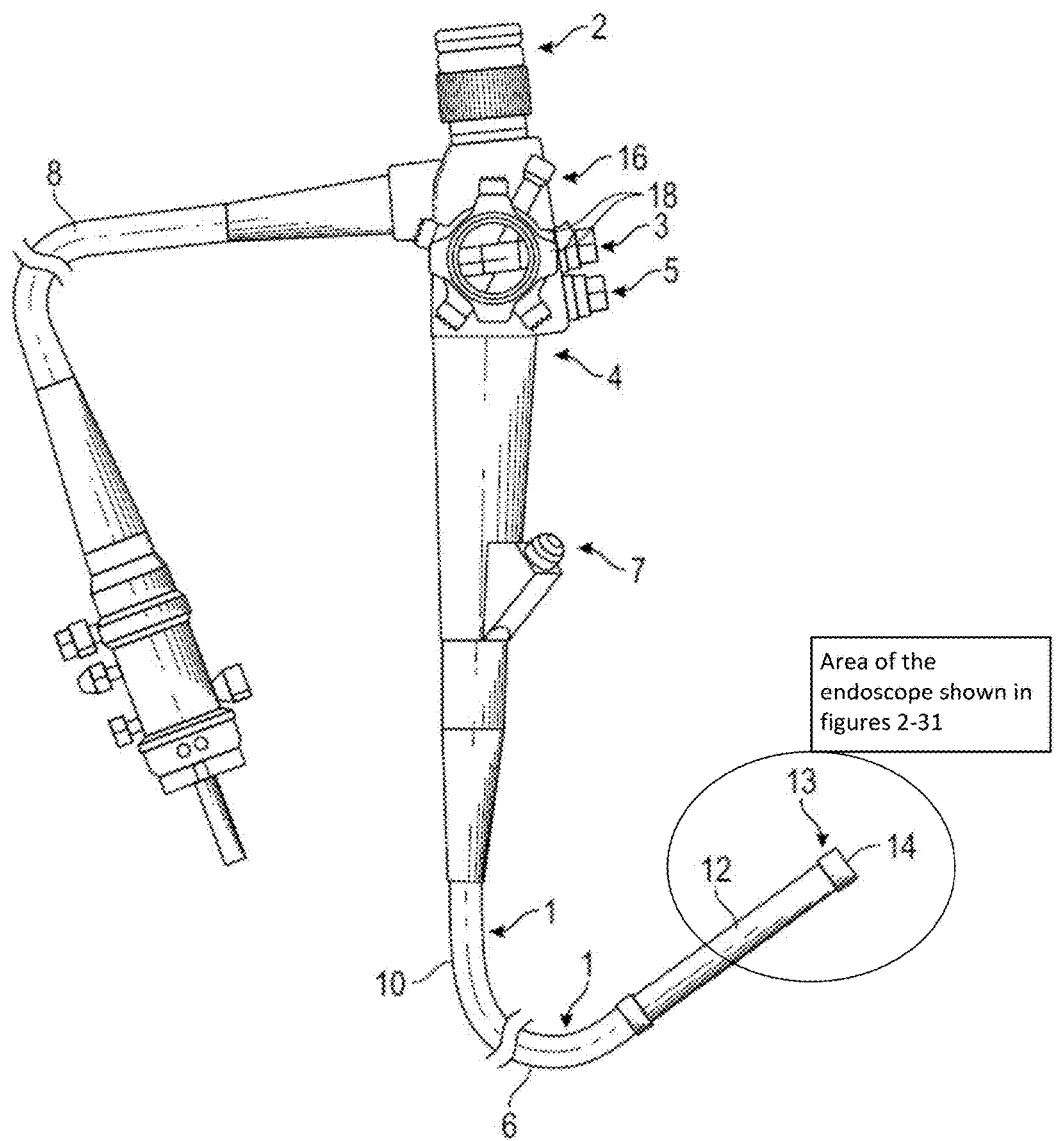
FIG. 1 shows a view of a conventional endoscope.
Figure 2:
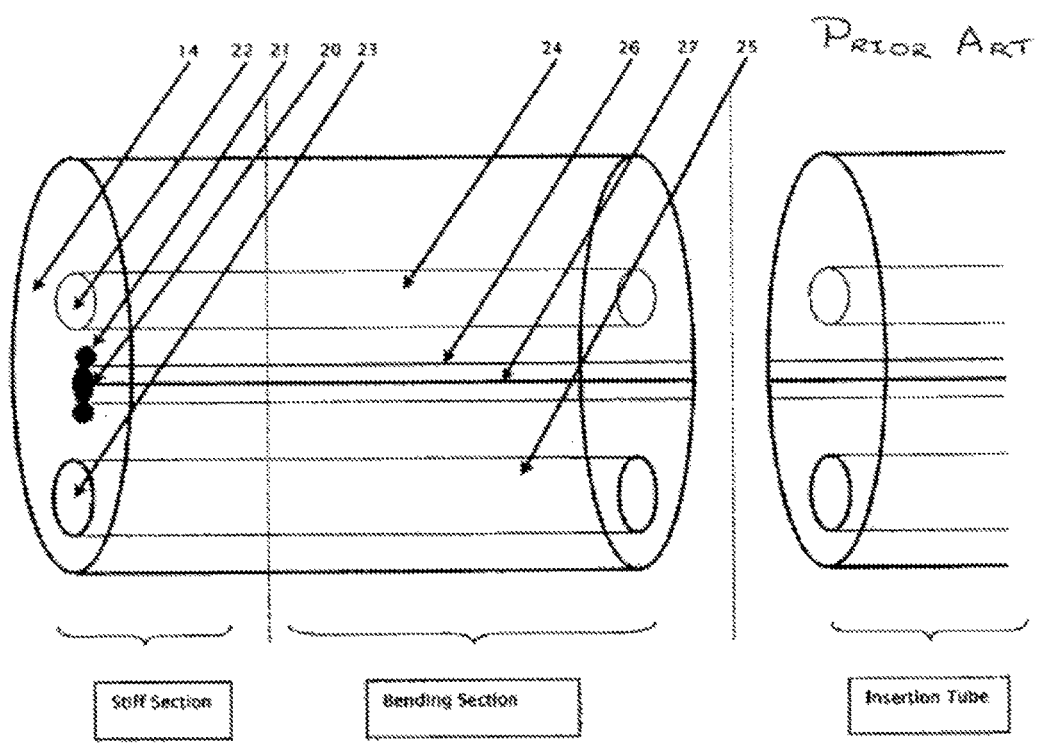
FIG. 2 shows a side view of the distal end, bending section and insertion tube of a conventional endoscope.

FIGS. 1 and 2 illustrate an embodiment of a conventional endoscope. It has a handle (4) from which extends a flexible shaft (1), which is inserted into a hollow organ to be inspected. The shaft consists of a proximal section (10), insertion tube (6), bending section (12) and a stiff section (13). The shaft terminates in the distal end (14), which typically houses one image lens (20), one to two illumination bulbs (21), air/water nozzle (22) and an instrument channel outlet (23). Light is transmitted from a light source through the shaft via an electric cable (26) to the illumination bulb (21). The illumination bulb illuminates the area to be examined. The image lens (20) captures images of the illuminated area. The image is then transmitted through a fiber optic cable (27) and viewed through an eyepiece (2) attached to the handle of the endoscope. Alternatively, the image is converted to a video signal and is then transmitted to an image processor by an electrical cable. The image is processed and displayed on a display unit like a computer monitor (not shown). The handle (4) of the endoscope has a grip (16) and an extension arm (8) that attaches the endoscope to a light source and an image processor.

To enable the endoscope to maneuver through the turns of a hollow organ the shaft is flexible and incorporates a multitude of wires that attach the bending portion (12) with actuators (18). Typically, there are two pairs of such wires passing within the shaft, one pair for flexing the bending portion in one plane and the other pair for flexing it in an orthogonal plane. Tension is applied to these wires using the actuators (18) to move the bending portion (12) in various directions.

It is also usual to provide two channels extending between the handle and the distal end of the shaft, an air/water channel (24) and an instrument channel (25). The air/water channel (24) is used to insufflate air in a hollow organ to expand it for proper visualization. The air/water channel is connected proximally to an air/water pump (not shown) and to distally to the air/water nozzle (22). It is controlled by an air/water control valve (5) located on the handle (4). The image lens (20) and the illumination bulb (21) are frequently smeared with blood, stool or other body fluids while in a hollow organ. In such a situation, the air/water channel (24) is used to squirt water or blow air at the image lens (20) and/or illumination bulb (21) in order to clean them while still inside a hollow organ. The instrument channel (25) has an instrument channel inlet (7) proximally and an instrument channel outlet (23) distally. It is used to pass surgical instruments to do various surgical procedures. It is also used to apply suction using the suction control valve (3) located on the handle (4). This suction is useful in removing fluids, air and other materials from within a hollow organ during examination.

Figure 3:
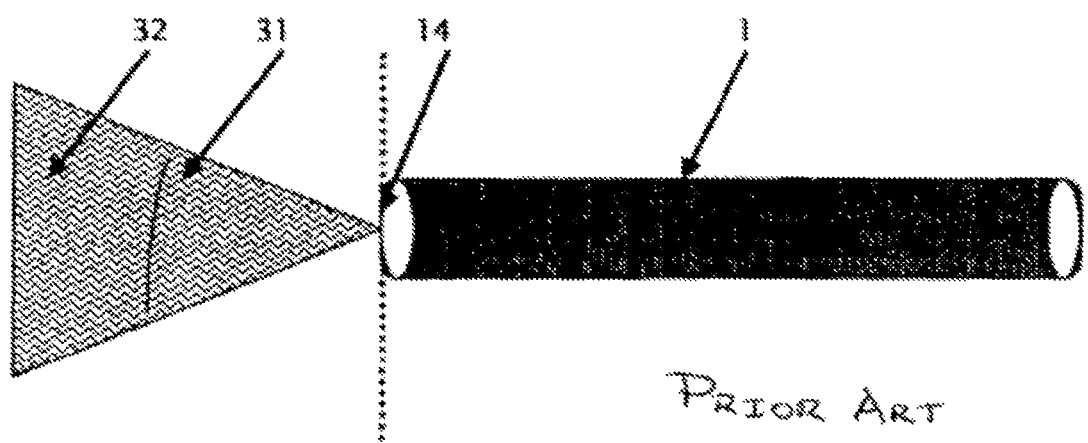
FIG. 3 is a side view of a conventional endoscope displaying the field of vision of a conventional endoscope.

FIG. 3 illustrates the narrow field of vision (31) of about 120 degrees of a conventional endoscope (1). It also shows that conventional endoscopes are only forward viewing (32).

Figure 4A:
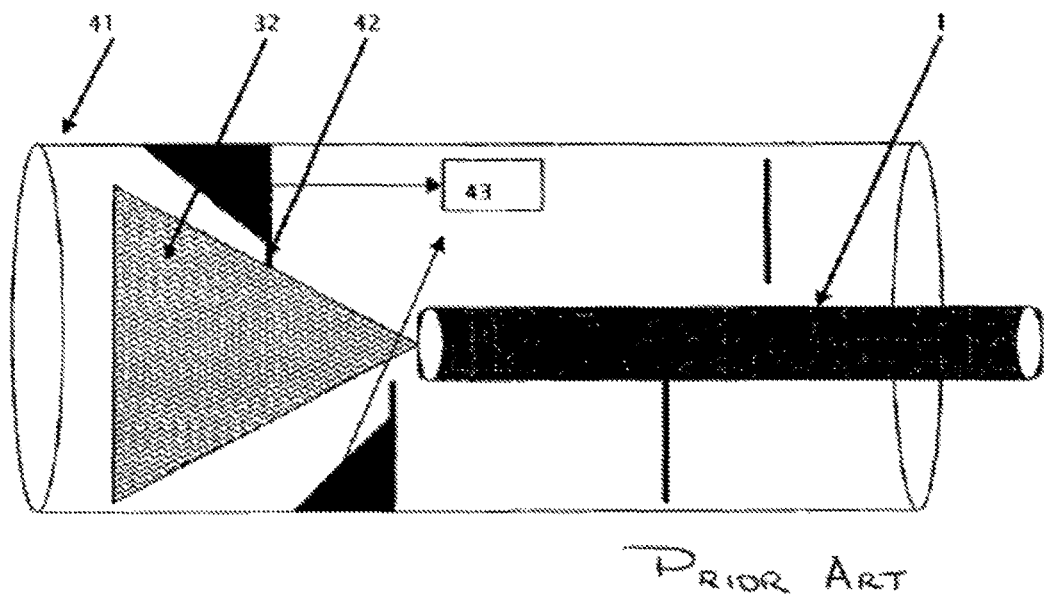
FIG. 4A shows a conventional endoscope inside a colon. It shows mucosal folds of the colon and illustrates that visualization of the area behind mucosal folds is obstructed by the front of the mucosal folds during examination with a conventional endoscope.

FIG. 4A shows side view of an endoscope (1) inside colon (41). The colon has mucosal folds (42). The front side of a mucosal fold blocks the view of the areas behind it during a typical endoscopic examination. These areas form the 'blind spots' (43) of a conventional endoscope that lie outside of the forward field of vision (32).

Figure 4B:
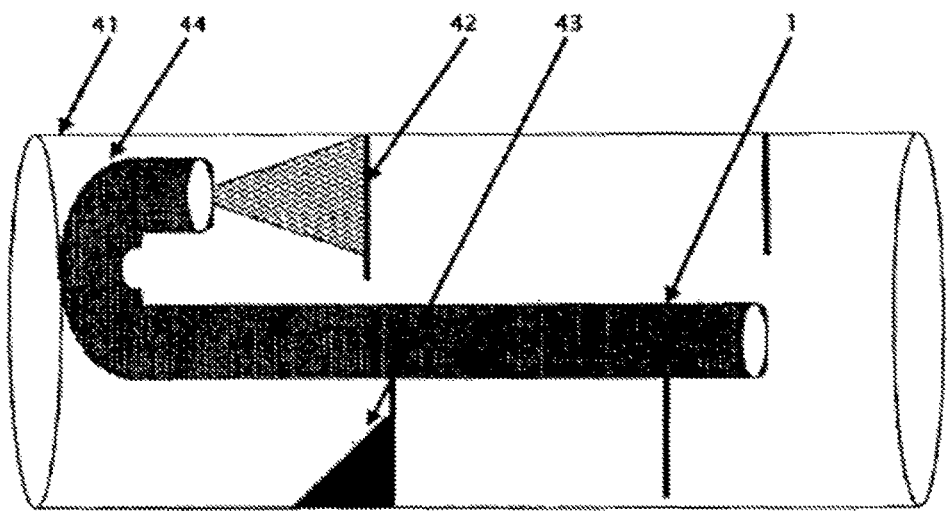
FIG. 4B shows a conventional endoscope inside a colon in a retroflexed position. It displays how retro flexion enables visualization of area behind a mucosal fold.

FIG. 4B shows side view of the retro flexion maneuver (44) of a conventional endoscope (1) inside colon (41). During this maneuver, the endoscope is advanced beyond the mucosal fold (42) to be examined. The bending portion of the endoscope is then bent to 180 degrees to visualize the rear side of a mucosal fold (43) during forward examination, the view of which is obstructed by its front side during a forward examination.

Figure 5:
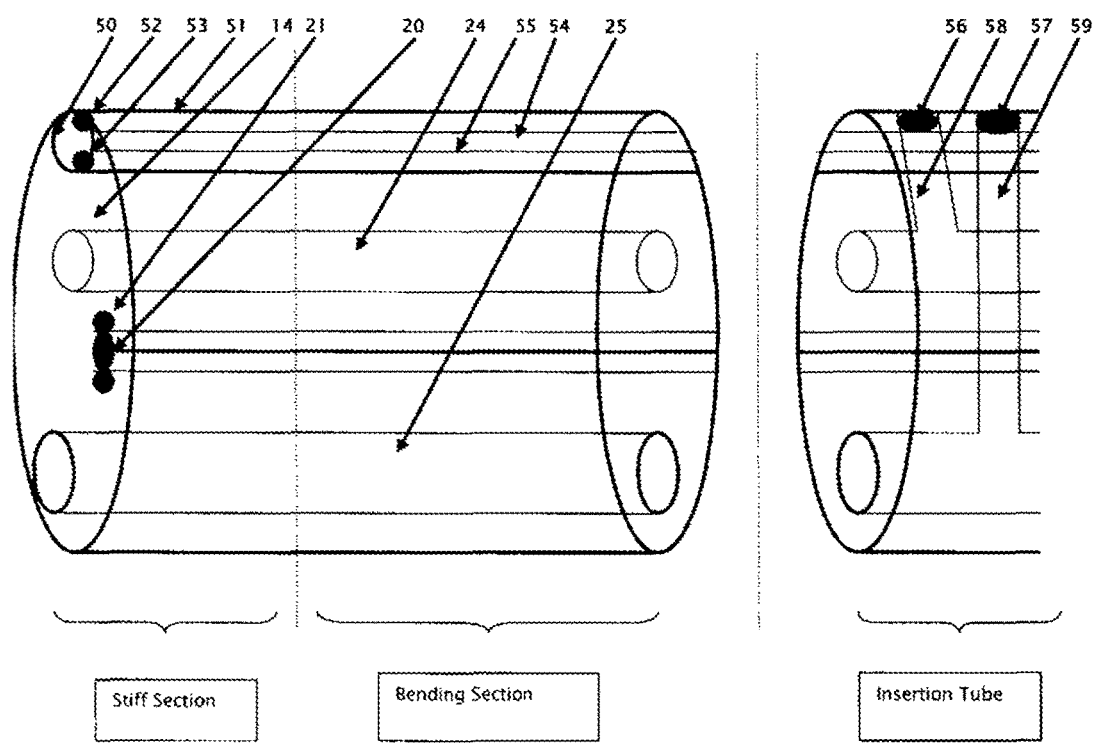
FIG. 5 shows side view of an endoscope with the 'rear view module' according to a first embodiment of the present invention.

FIG. 5 shows side view of a first preferred embodiment of the present invention. The rear view module (51) is a long thin tubular structure encased in a sheath. It is placed along the periphery of a conventional endoscope. In the preferred embodiment, the rear view module (51) extends through the entire length of the endoscope but it may be shorter. The rear view module (51) has a distal end (50), stiff section, bending section and proximal section similar to an endoscope. In the preferred embodiment, the distal end (50), stiff section, bending section and proximal section of the rear view module (51) is in sync with the distal end (14), stiff section, bending section and proximal section of a conventional endoscope. The distal end (50) of the rear view module has a rear image lens (52) and a rear illumination bulb (53). The rear image lens (52) is connected to an image processor (not shown) and the rear illumination bulb (53) is connected to a power source (not shown) by electrical cables (54, 55) that run within the rear view module (51). Two pairs of cables within the rear view module attach the bending section of the rear view module to a rear view module actuator. Tension on these cables moves the bending section of the rear view module in vertical and horizontal planes.

In the preferred embodiment, there is a rear air/water channel (58) with a rear air/water nozzle (56) and rear instrument channel (59) with a rear instrument channel outlet (57) located proximal to the bending section of the rear view module (51). The rear air/water channel (58) provides a jet of water and a stream of air that is used to clean the rear image lens (52) and the rear illumination bulb (53). It is also used to insufflate air in the field of vision of the rear image lens (52) for better distension and visualization. Surgical instruments are passed through the rear instrument channel (59) to do various surgical procedures in the area under view of the rear image lens (52). It is also used to direct suction to the area under the view of the rear image lens (52).

In the preferred embodiment, the rear air/water channel (58) and the rear instrument channel (59) is connected to the main air/water channel (24) and the main instrument channel (25) respectively. However, these may exist independently. Passage to the rear air/water channel (58) and rear instrument channel (59) from the main air/water channel (24) and main instrument channel (25) is controlled by a valve or any other suitable mechanical device. Typically, deployment of the rear view module (51) automatically opens the passage to the rear air/water channel (58) and the rear instrument channel (59). Alternatively, the passageways can be controlled independently.

According to another aspect of the preferred embodiment, there can be more than one rear view module.

Figure 6:
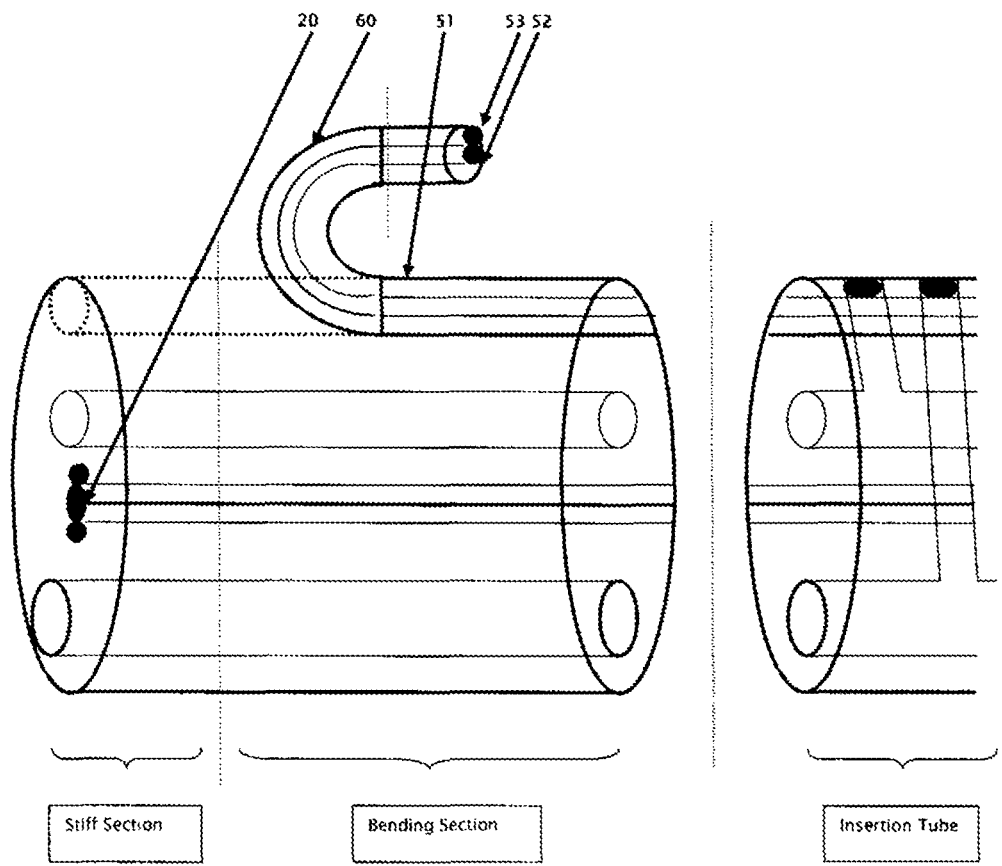
FIG. 6 shows side view of the endoscope in FIG. 5 wherein the 'rear view module' is deployed for rear view.

FIG. 6 shows the preferred embodiment in FIG. 5 where the rear view module (51) is retro flexed (60) using the rear view module actuator. With this maneuver, the rear image lens (52) faces backward and provides a rear view. The rear illumination bulb (53) illuminates the area under view of the rear image lens (52). The main image lens of the endoscope (20) provides a front view at the same time when the rear image lens (52) is providing a rear view. However, the operator may choose to have only one view at a given time. Because the rear view module is thin, retro flexion can be achieved with a small radius of curvature and thus can be performed even inside narrow hollow organs.

Figure 7:
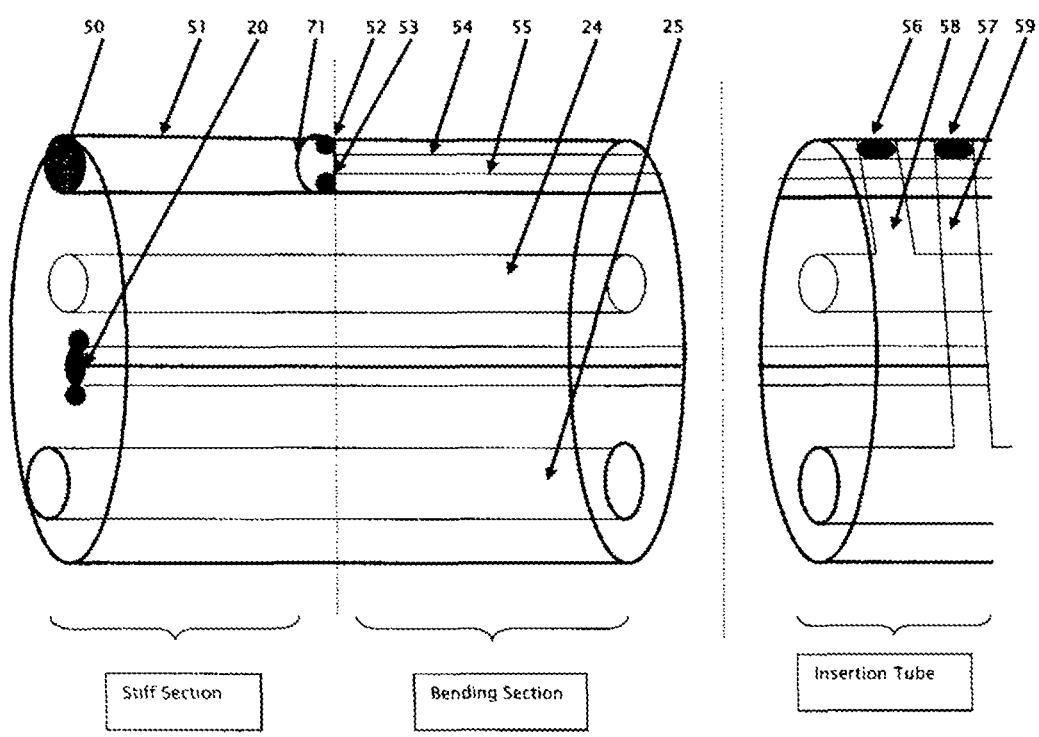
FIG. 7 shows side view of an endoscope with the 'rear view module' according to a second embodiment of the present invention.

FIG. 7 shows side view of a second preferred embodiment of the present invention. The rear view module (51) is a solid rectangular block with a proximal end (71) and a distal end (50). It is located within the stiff section of the endoscope. The rear image lens (52) and the rear illumination bulb (53) are located on the proximal end (71) of the rear view module. The rear image lens (52) is connected to an image processor and the rear illumination bulb (53) is connected to a power source by electric cables (54, 55). The distal end (50) of the rear view module is attached to the distal end (14) of the endoscope by a hinge joint or any other suitable mechanical articulation. The distal end (50) of the rear view module is connected to a rear view module actuator by a pair of cables (not shown). Tension on these cables moves the rear view module away from and towards the shaft of the endoscope as shown in FIG. 8.

In the preferred embodiment, there is a rear air/water channel (58) with a rear air/water nozzle (56) and rear instrument channel (59) with a rear instrument channel outlet (57) located proximal to the rear view module (51). The rear air/water channel (58) provides a jet of water and a stream of air that is used to clean the rear image lens (52) and the rear illumination bulb (53). It is also used to insufflate air in the field of vision of the rear image lens (52) for better distension and visualization. Surgical instruments are passed through the rear instrument channel (25) to do various surgical procedures in the area under view of the rear image lens (52). It is also used to direct suction to the area under the view of the rear image lens (52).

In the preferred embodiment, the rear air/water channel (58) and the rear instrument channel (59) is connected to the main air/water channel (24) and the main instrument channel (25) respectively. However, these may exist independently. Passage to the rear air/water channel (58) and rear instrument channel (59) from the main air/water channel (24) and main instrument channel (25) is controlled by a valve or any other suitable mechanical device. Typically, deployment of the rear view module (51) automatically opens the passage to the rear air/water channel (58) and the rear instrument channel (59). Alternatively, the passageways can be controlled independently.

Figure 8:
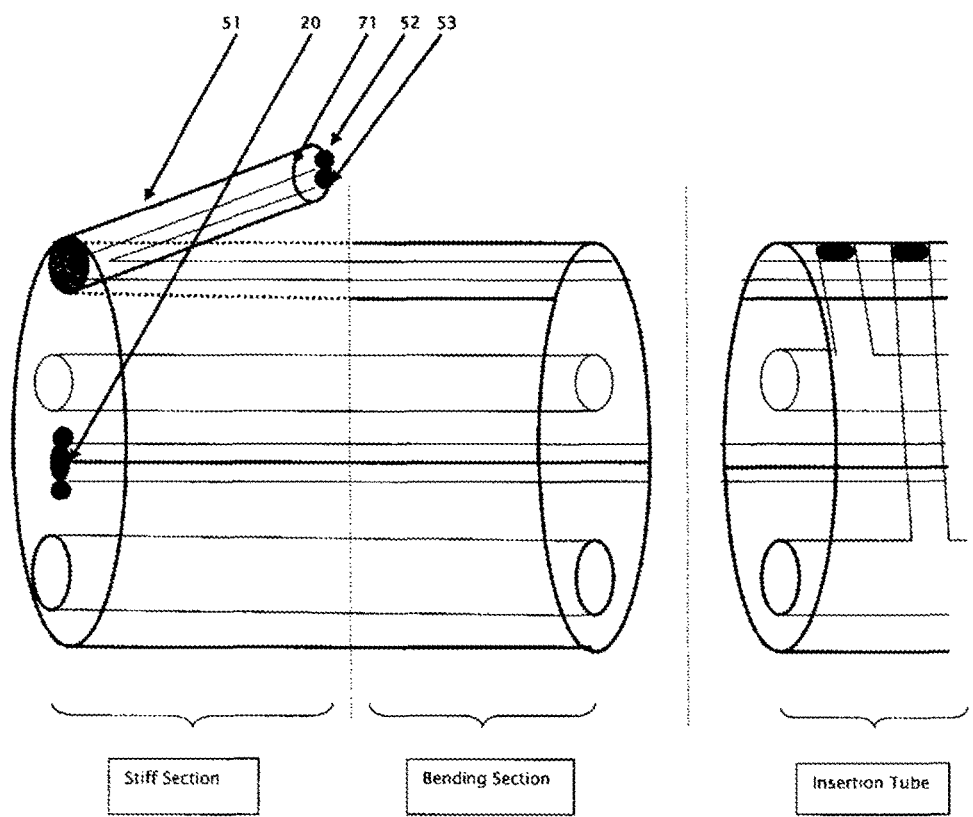
FIG. 8 shows side view of the endoscope in FIG. 7 wherein the 'rear view module' is deployed for rear view.

FIG. 8 is a side view of the endoscope in FIG. 7 where the rear view module (51) has been deployed by lifting its proximal end (71) away from the shaft using the rear view module actuator. When fully deployed, the rear image lens (52) and the rear illumination bulb (53) face backward. The image captured by the rear image lens (52) is transmitted to an image processor. The rear illumination bulb (53) illuminates the area under view of the rear image lens (52). The main image lens (20) is able to give a forward view at the same time as the rear image lens is giving a rear view. Forward and rear view can thus be obtained simultaneously if so desired by the operator. A major advantage of this embodiment is that it makes rear view possible requiring only minimal additional space. This is of particular advantage when examining narrow body cavities.

Figure 9:
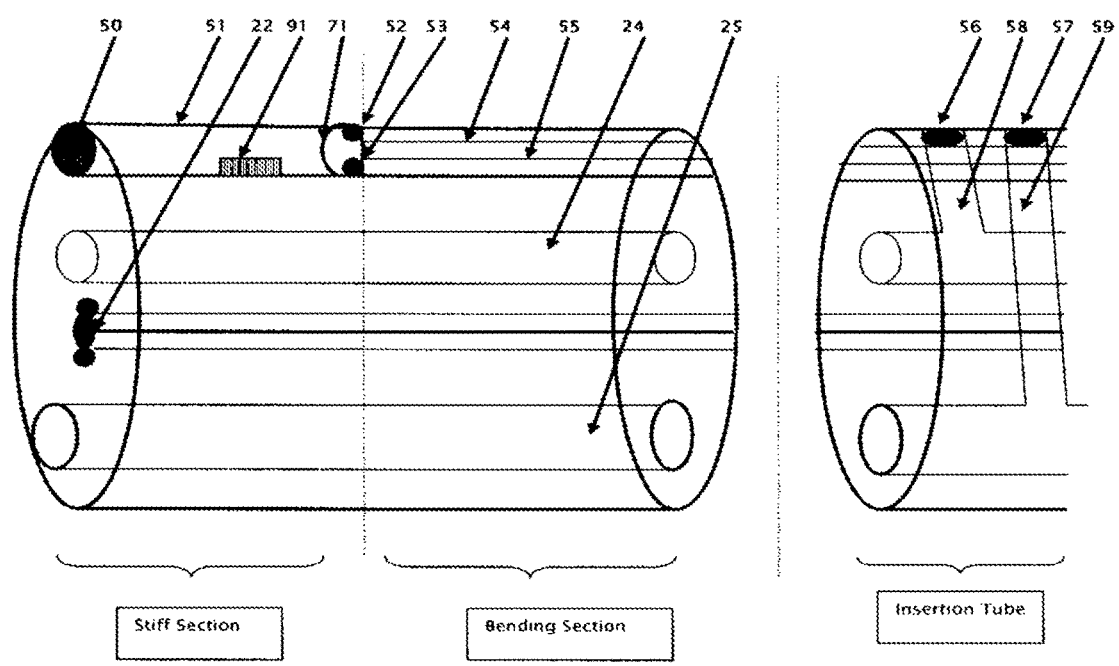
FIG. 9 shows side view of an endoscope with a 'rear view module' according to a third embodiment of the present invention.

FIG. 9 shows side view of a third preferred embodiment of the present invention. The rear view module (51) is a solid rectangular block with a proximal (71) and distal (50) end. It is located within the stiff section of the endoscope. The rear image lens (52) and the retro illumination bulb (53) are placed on the proximal end (71) of the rear view module. The rear image lens (52) is connected to an image processor and the rear illumination bulb (53) in connected to a power source by electric cables (54, 55). The rear view module rests on a support pillar/spring (91). The support pillar/spring can be extended and retracted perpendicular to the shaft of the endoscope. It is attached to a rear view module actuator by cables.

In the preferred embodiment, there is a rear air/water channel (58) with a rear air/water nozzle (56) and rear instrument channel (59) with a rear instrument channel outlet (57) located proximal to the rear view module (51). The rear air/water channel (58) provides a jet of water and a stream of air that is used to clean the rear image lens (52) and the rear illumination bulb (53). It is also used to insufflate air in the field of vision of the rear image lens (52)

for better distension and visualization. Surgical instruments are passed through the rear instrument channel (25) to do various surgical procedures in the area under view of the rear image lens (52). It is also used to direct suction to the area under the view of the rear image lens (52).

In the preferred embodiment, the rear air/water channel (58) and the rear instrument channel (59) is connected to the main air/water channel (24) and the main instrument channel (25) respectively. However, these may exist independently. Passage to the rear air/water channel (58) and rear instrument channel (59) from the main air/water channel (24) and main instrument channel (25) is controlled by a valve or any other suitable mechanical device. Typically, deployment of the rear view module (51) automatically opens the passage to the rear air/water channel (58) and the rear instrument channel (59). Alternatively, the passageways can be controlled independently.

Figure 10:
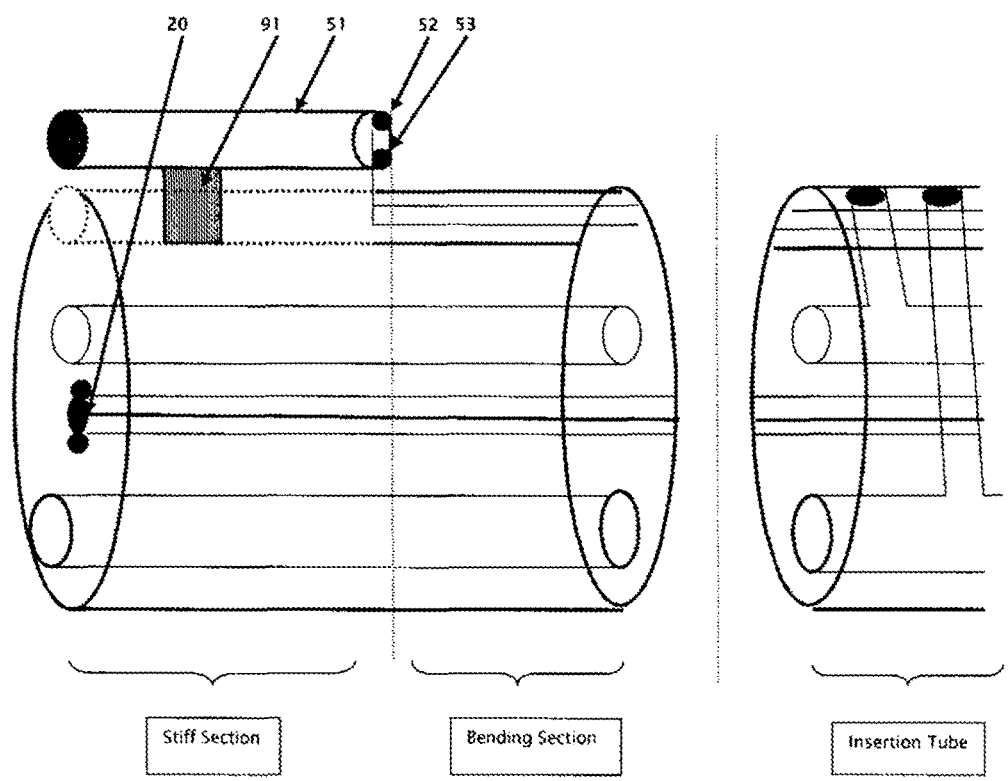
FIG. 10 is a side view of the endoscope in FIG. 9 wherein the 'rear view module' is deployed for rear view.

FIG. 10 shows the endoscope in FIG. 9 where it has been deployed by moving the support pillar/spring (91) vertically from the shaft using the rear view module actuator. In this position, the rear image lens (52) and the rear illumination bulb (53) face backward. The rear image lens (52) provides a rear view and the rear illumination bulb (53) illuminates the area under the view of the rear image lens (52). The main image lens (20) is able to provide a forward view at the same time when the rear image lens (52) is providing a rear view. This enables simultaneous forward and rear view if so chosen by the operator. A major advantage of this embodiment is that it provides a straight rear view that is desirable for certain surgical procedures.

Figure 11:
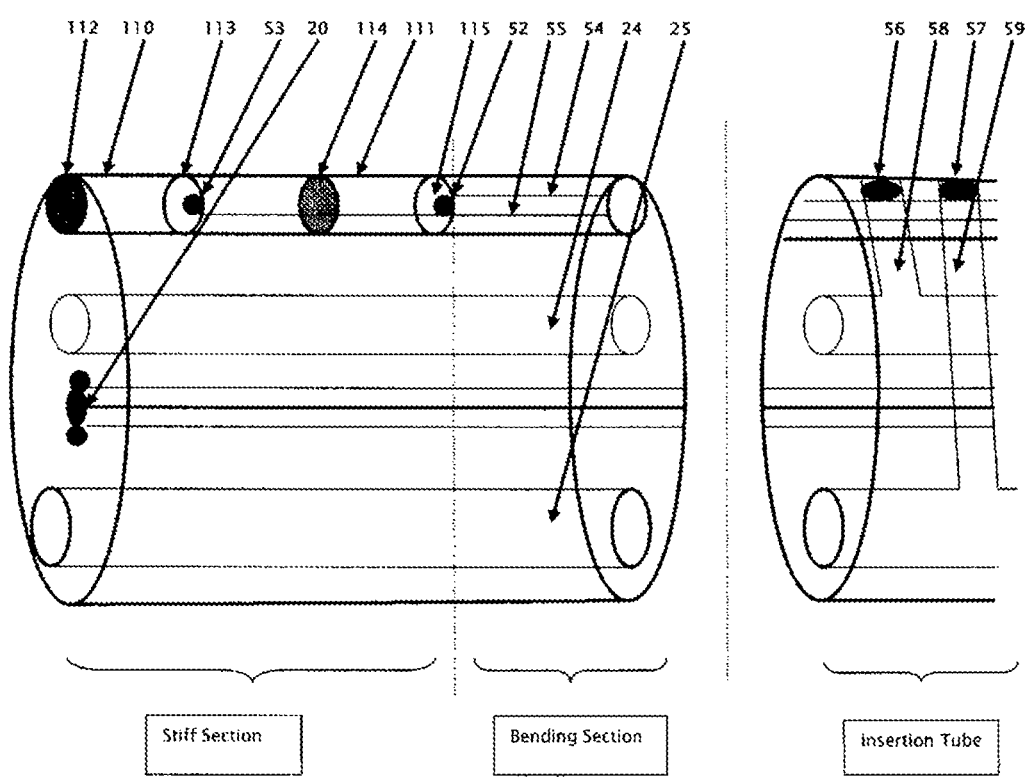
FIG. 11 shows side view of an endoscope with a 'rear view module' according to a fourth embodiment of the present invention.

FIG. 11 shows a side view of a fourth preferred embodiment of the present invention. The rear view module (51) is made of two sub modules, the rear image module (111) and the rear illumination module (110). The sub modules are small rectangular solid structures. They are placed within the stiff section of the endoscope. The retro image module contains the rear image lens (52) and the rear illumination module contains the rear illumination bulb (53). The rear image lens (52) is placed on the proximal end (115) of the rear image module (110) and the rear illumination bulb (53) is placed on the proximal end (113) of the retro illumination module (111). The rear image lens (52) is connected to an image processor by an electric cable (54) and the rear illumination bulb (53) is connected to a power source by an electric cable (55).

Figure 12:
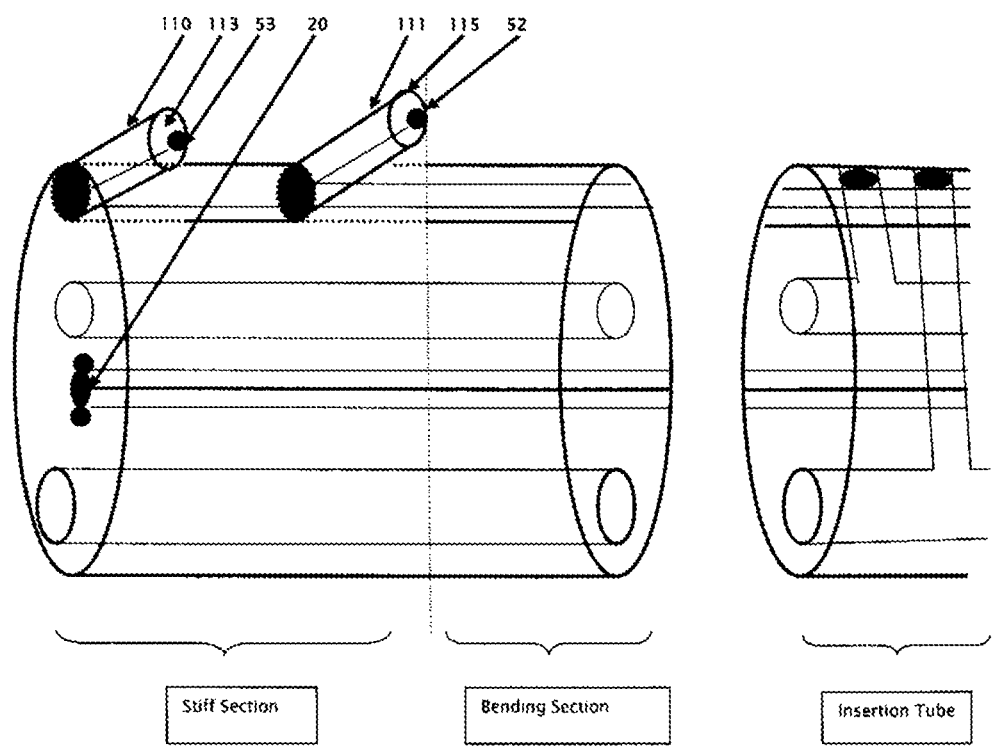
FIG. 12 shows side view of the endoscope in FIG. 11 wherein the 'rear view module' is deployed for rear view.

In the preferred embodiment, the rear image module (111) and the rear illumination module (110) are embedded within the stiff section of the endoscope. The distal end (114) of the rear image module and the distal end (112) of the rear illumination module are attached to the shaft of the endoscope by a hinge joint or any other suitable mechanical articulation. The distal ends of the rear image module and of the rear illumination module (112, 114) are also connected to a pair of rear view module actuators by cables. Tension on these cables moves the rear image module (111) and rear illumination module (110) away from and towards the shaft as shown in FIG. 12. The rear image module (111) and the rear illumination module (110) are placed at a suitable distance from each other.

In the preferred embodiment, there is a rear air/water channel (58) with a rear air/water nozzle (56) and rear instrument channel (59) with a rear instrument channel outlet (57) located proximal to the rear view module (51). The rear air/water channel (58) provides a jet of water and a stream of air that is used to clean the rear image lens (52) and the rear illumination bulb (53). It is also used to insufflate air in the field of vision of the rear image lens (52) for better distension and visualization. Surgical instruments are passed through the rear instrument channel (25) to do various surgical procedures in the area under view of the rear image lens (52). It is also used to direct suction to the area under the view of the rear image lens (52).

In the preferred embodiment, the rear air/water channel (58) and the rear instrument channel (59) is connected to the main air/water channel (24) and the main instrument channel (25) respectively. However, these may exist independently. Passage to the rear air/water channel (58) and rear instrument channel (59) from the main air/water channel (24) and main instrument channel (25) is controlled by a valve or any other suitable mechanical device. Typically, deployment of the rear view module (51) automatically opens the passage to the rear air/water channel (58) and the rear instrument channel (59). Alternatively, the passageways can be controlled independently.

According to another aspect of the preferred embodiment the relative positions of the rear illumination module and the rear image module can be interchanged. According to another aspect of the preferred embodiment more than one rear illumination module and/or rear image module can be present.

FIG. 12 is a side view of the endoscope in FIG. 11 where the retro image module (111) and the retro illumination module (110) have been deployed by moving their proximal ends (113,115) away from the shaft using the rear view module actuators. In this position the rear image lens (52) and the rear illumination bulb (53) face backward and provide a rear view. The main image lens (20) is able to provide a front view at the same time when the rear image lens is providing a rear view thus enabling a simultaneous front and rear view. A major advantage of the preferred embodiment is that the rear illumination module (110) can be controlled independent of the rear image module (111). This may be desirable in certain situations.

Figure 13:
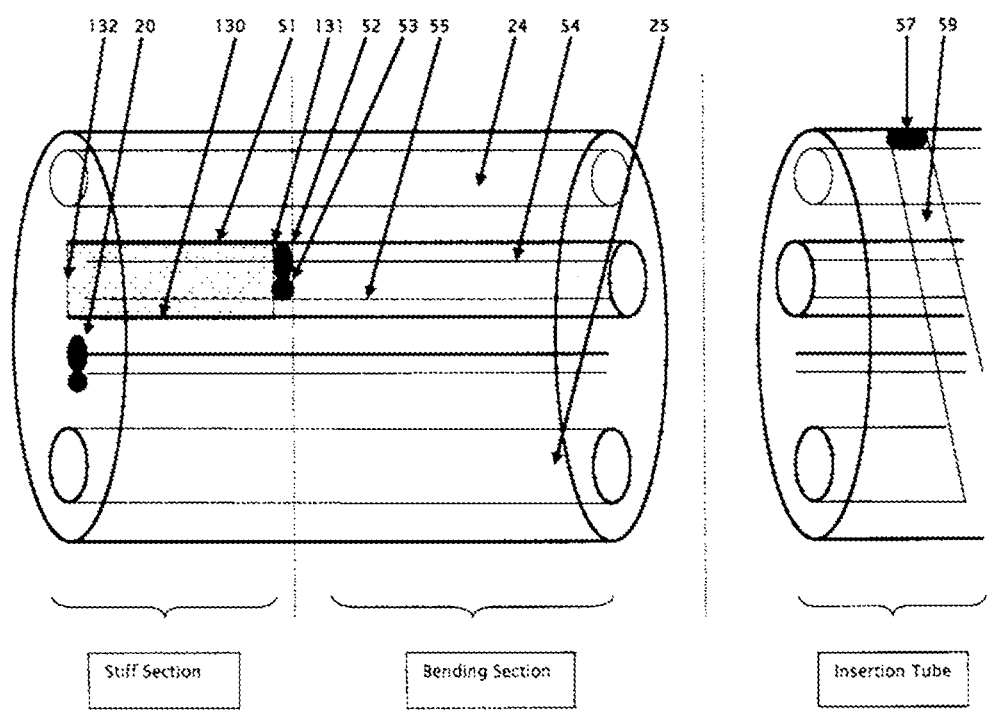
FIG. 13 shows side view of an endoscope with a 'rear view module' according to a fifth embodiment of the present invention.

FIG. 13 shows a side view of a fifth preferred embodiment of the present invention. The rear view module (51) is a solid rectangular block with a proximal (131) and distal ends (132). It is located within the stiff section of the endoscope. It contains a rear image lens (52) and a rear illumination bulb (53) placed on the proximal end (131) of the rear view module. The rear image lens (52) is connected to an image processor by an electric cable (54). The rear illumination bulb (53) is connected to the power source by an electric cable (55). The rear view module (51) rests on a support arm (130) within the stiff section of the endoscope. The support arm (130) also serves as an extension arm that can be extended, retracted and rotated. The distal end (132) of the rear view module is attached to the support arm (130) by a hinge joint or any other suitable mechanical articulation. It is also connected to a rear view module actuator by cables. Tension on these cables moves the rear view module (51) away from and towards the support arm (130).

In the preferred embodiment, there is a rear instrument channel (59) with a rear instrument channel outlet (57) located proximal to the rear view module (51). It is used to pass surgical instruments to do various surgical procedures in areas under view of the rear image lens (52). It is also used to direct suction to the area under the view of the rear image lens (52). The main air/water channel (24) is used to clean the rear image lens (52) and the rear illumination bulb (53).

In the preferred embodiment, the rear instrument channel (59) is connected to the main instrument channel (25). However, it may exist independently. Passage to the rear instrument channel (59) from the main instrument channel (25) is controlled by a valve or any other suitable mechanical device. Typically, deployment of the rear view module (51) will automatically open the passage to the rear instrument channel (59). Alternatively, the passageway can be controlled independently.

In the preferred embodiment, the rear view module is served by the main air/water channel (24). However a rear air/water channel may be provided. According to another aspect of the preferred embodiment, an additional forward image lens and an additional forward illumination bulb can be present at the distal end (132) of the rear view module. This will widen the forward field of vision. According to another aspect of the present invention, more than one rear view module can be present.

Figure 14:
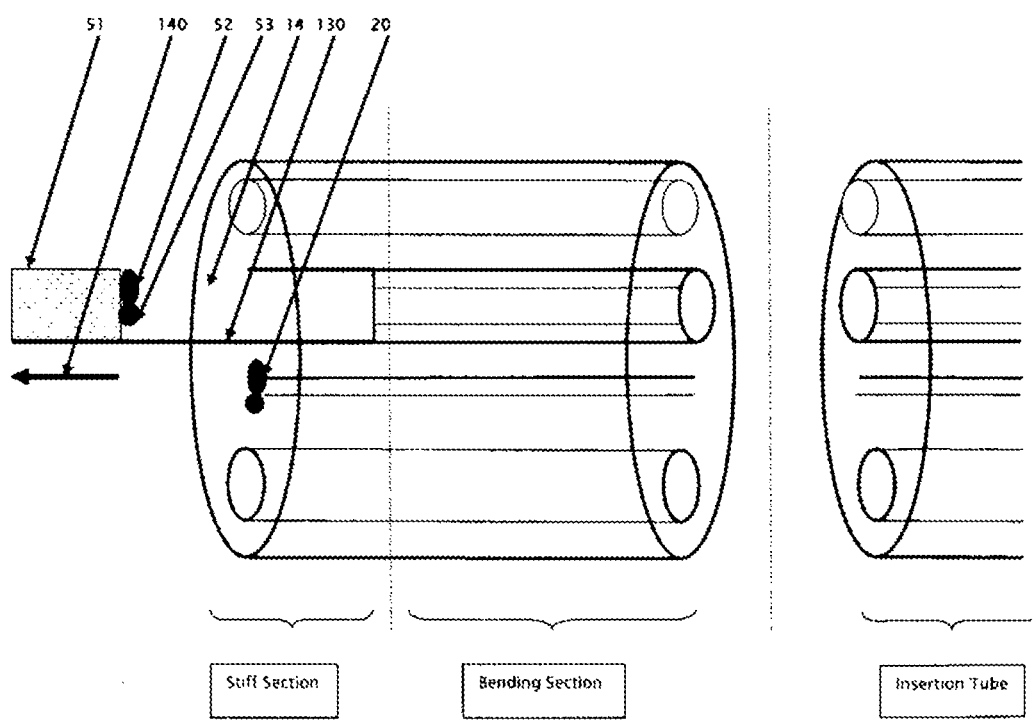
FIGS. 14-16 is a side view of the endoscope in FIG. 13 wherein the 'rear view module' is deployed for rear view.
Figure 15:
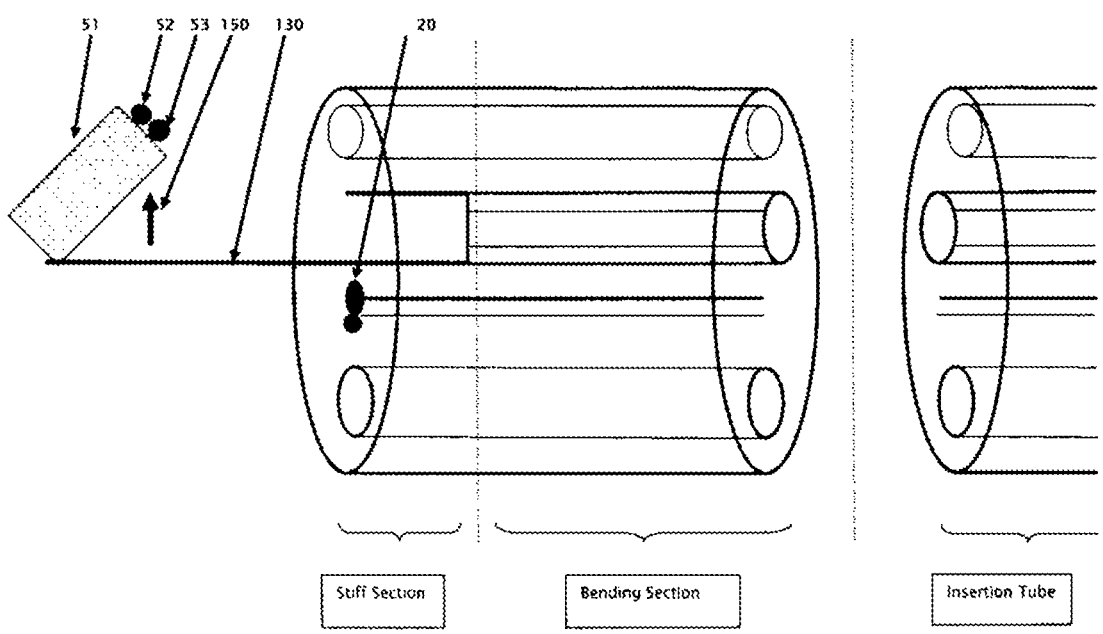
Figure 16:
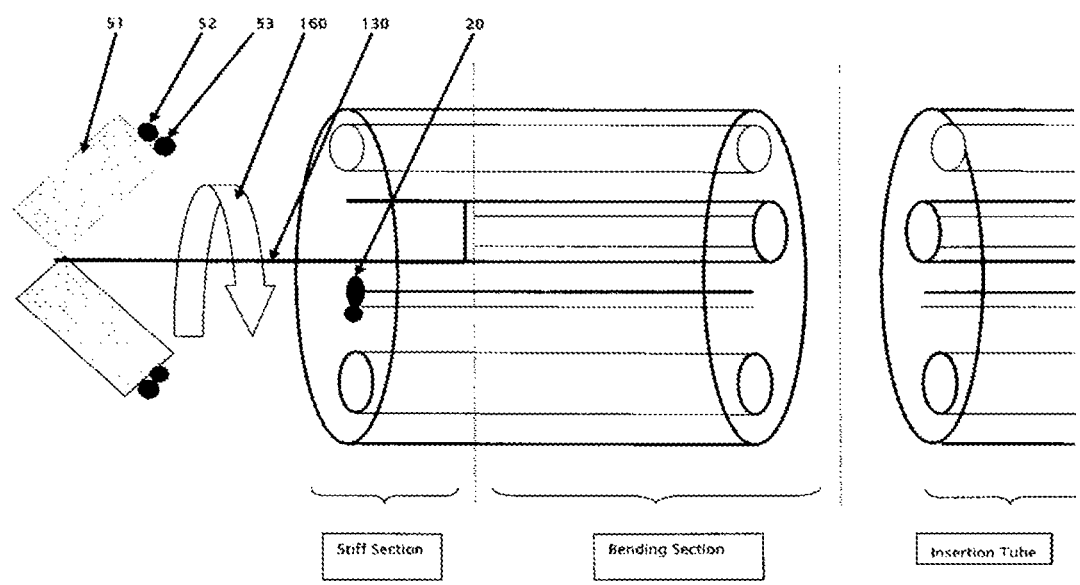

FIG. 14-16 shows side view of the endoscope in FIG. 13 where the rear view module (51) has been deployed for rear view. The support arm (130) is extended forward (140) to an appropriate distance from the distal end (14) of the endoscope as shown in FIG. 14. The rear image lens (52) faces backward in this position and gives a rear view. The rear illumination bulb (53) faces backward and illuminates the area under view of the rear image lens (52). The main image lens (20) is able to give a front view at the same time as the rear image lens (52) is giving a rear view, thus enabling simultaneous front and rear views. The rear view module (51) can be lifted from (150) and retracted towards the support arm (130) using the rear view module actuator as shown in FIG. 15. In addition, the support arm can be rotated (160) as shown in FIG. 16. This increases the rear field of vision.

Figure 17:
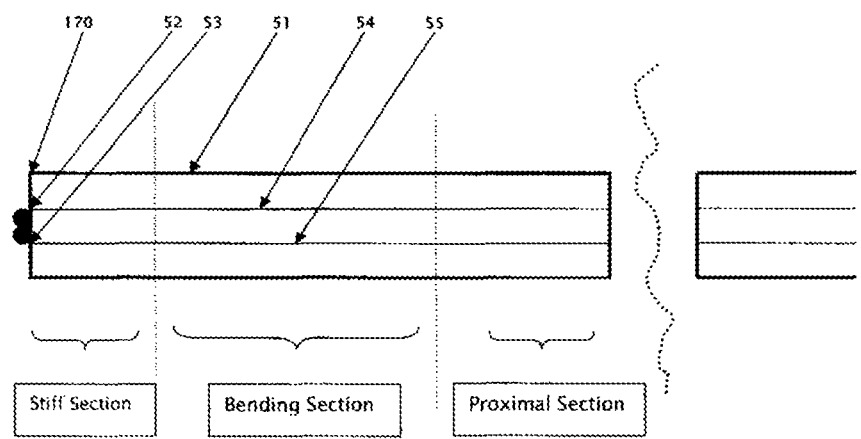
FIG. 17 shows side view of a 'rear view module' according to a sixth embodiment of the present invention.

FIG. 17 shows side view of a sixth preferred embodiment of the present invention. The rear view module (51) is a long and thin tubular structure encased in a sheath. It has a shaft that comprises of a distal end (170), stiff section, bending section and proximal section. The shaft is attached proximally to a handle (not shown). The handle has an extension that connects the rear view module (51) to an image processor and a power source. Rear image lens (52) and rear illumination bulb (53) are placed on the distal end (170) of the rear view module (51). The rear image lens (52) and the rear illumination bulb (53) are connected to an image processor and a light source respectively by electrical cables (54, 55). The bending section of the rear view module is connected to a rear view module actuator by cables. Tension on these cables moves the bending section in vertical and horizontal planes. This entire assembly is thin enough to pass through the main instrument channel (25) of the endoscope.

Figure 18:
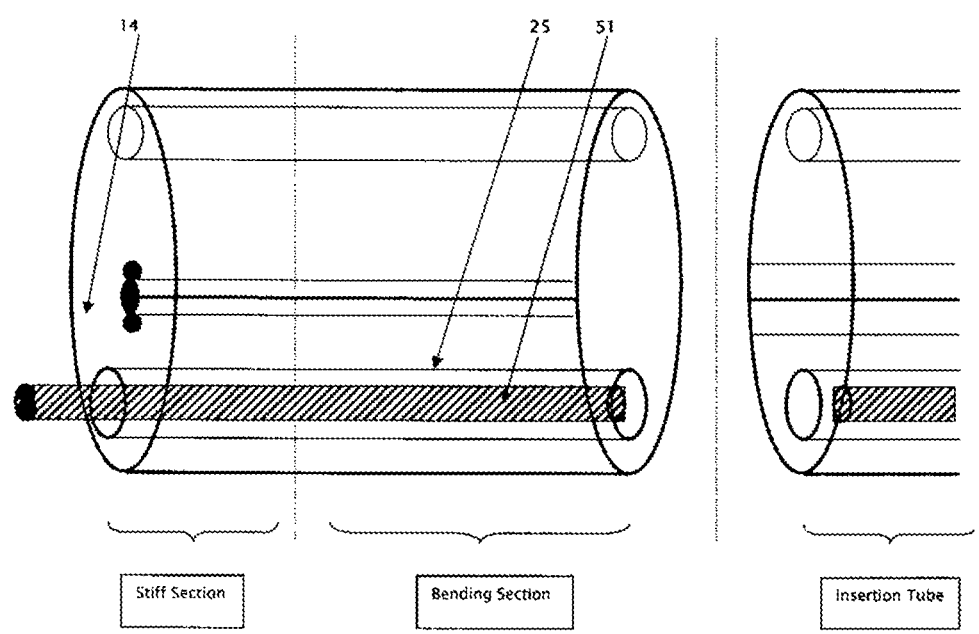
FIGS. 18 & 19 shows side view of the endoscope in FIG. 17 wherein the 'rear view module' is deployed for rear view.
Figure 19:
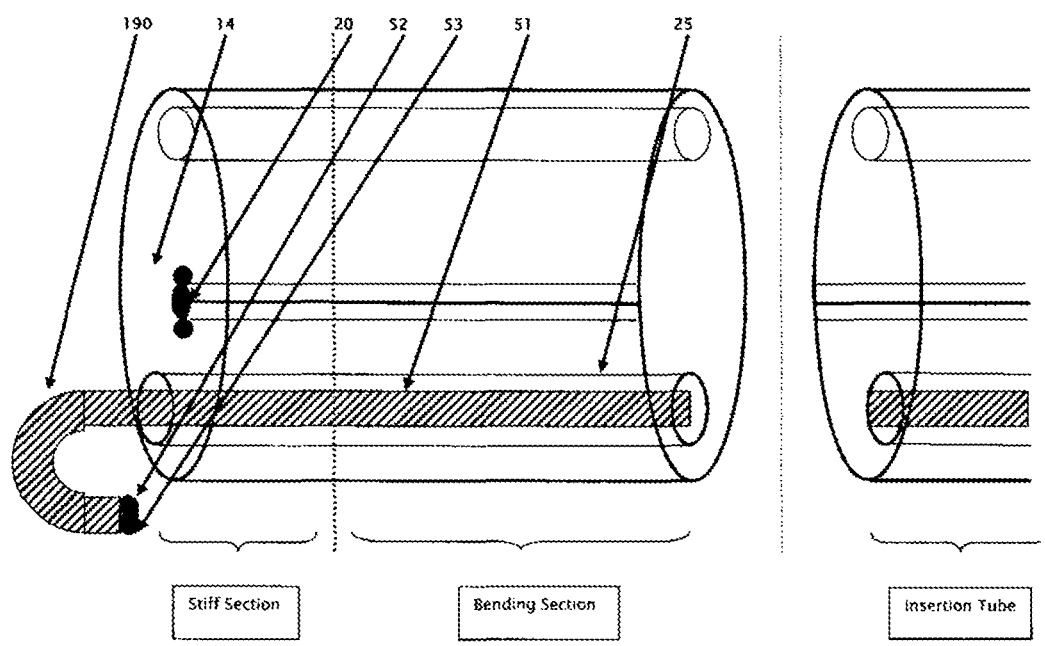

The rear view module (51) is passed through the instrument channel (25) beyond the distal end (14) of the endoscope as shown in FIG. 18. Backward view is obtained by retro flexing (190) the bending portion of the rear view module (51) as shown in FIG. 19. In this position, the rear image lens (52) and the rear illumination bulb (53) face backward. The rear image lens (52) gives a rear view and the rear illumination bulb (53) illuminates the area under the view of the rear image lens (52). The main image lens (20) is able to give a forward view at the same time as the rear image lens (52) is giving a rear view. Simultaneous forward and rear view can thus be obtained if desired by the operator. The rear image lens (52) and the rear illumination bulb (53) is serviced by the main air/water channel (24).

In a variation of the preferred embodiment, it can have a rear air/water channel and/or a rear instrument channel. In another variation to the preferred embodiment, the rear view module (51) can be passed through the rear instrument channel if one is present. In another variation of the preferred embodiment, the rear view module is embedded within the shaft of the endoscope. It is extended beyond the distal end of the endoscope and then retro flexed/bent to give a rear view.

Figure 20:
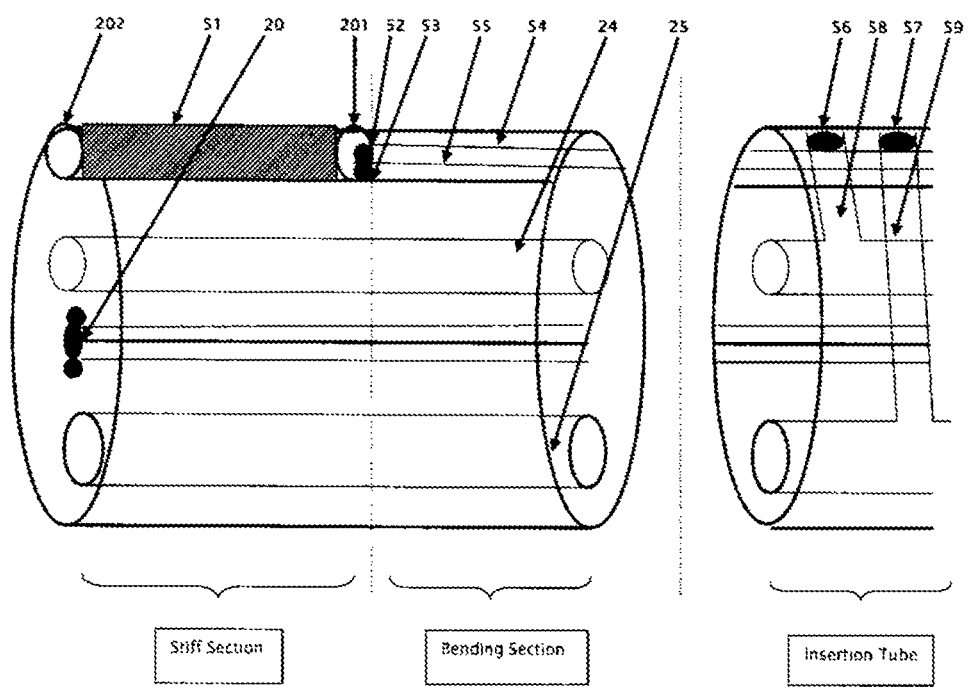
FIG. 20 shows side view of an endoscope with a 'rear view module' according to a seventh embodiment of the present invention.
Figure 21:
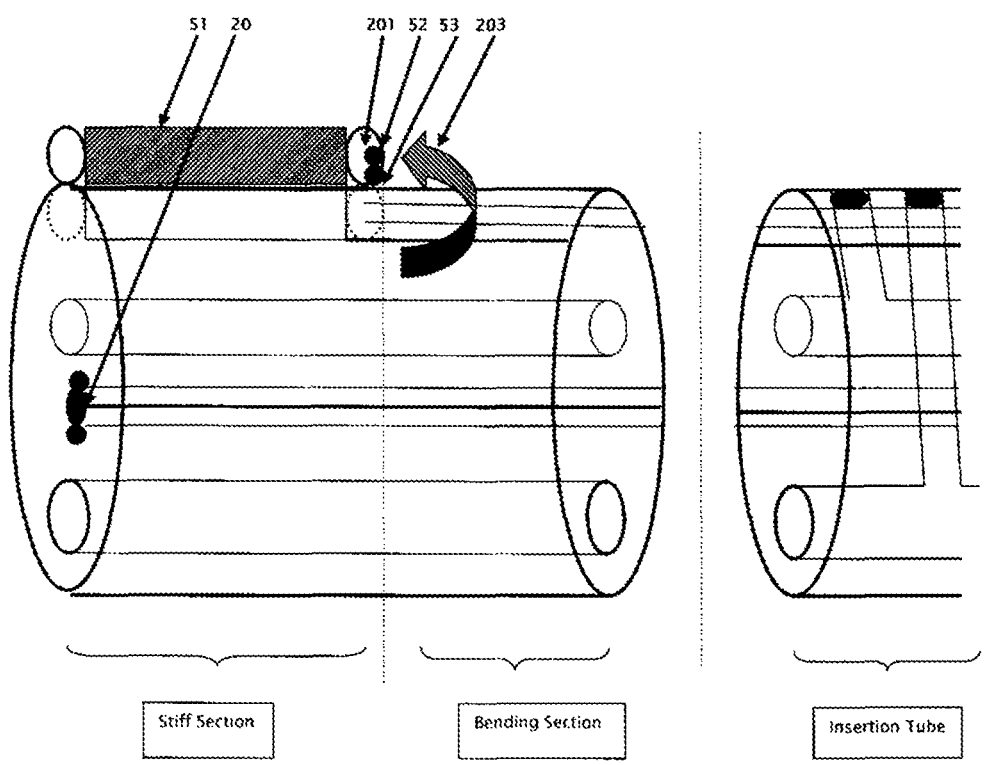
FIG. 21 is a side view of the endoscope in FIG. 20 wherein the 'rear view module' is deployed for rear view.

FIG. 20 shows side view of a seventh preferred embodiment of the present invention. The rear view module (51) is a hollow tubular structure with a proximal end (201) and a distal end (202). It is placed within the peripheral part of the stiff section of the endoscope, parallel to its long axis. The rear view module (51) is connected along its length to the stiff section of the endoscope by a hinge joint or any other suitable mechanical articulation. The rear image lens (52) and the rear illumination bulb (53) are placed on the proximal end (201) of the rear view module. The rear image lens (52) is connected to an image processor and the rear illumination bulb (53) is connected to a power source by electric cables (54, 55). Two pairs of cables one on the outside and the other on the inside, connect the rear view module to an actuator along its length. Tension on these cables opens and closes the module like the lid of a box (203) as shown in FIG. 21. When opened, the rear image lens (52) and the rear illumination bulb (53) face backward. The rear image lens (52) gives a rear view and the rear illumination bulb (53) illuminates the area under view of the rear image lens (52). The main image lens (20) of the endoscope is able to give a forward view at the same time as the rear image lens (52) is giving a rear view. Hence, simultaneous forward and rear view is possible if the operator so desires.

In the preferred embodiment, there is a rear air/water channel (58) with a rear air/water nozzle (56) and rear instrument channel (59) with a rear instrument channel outlet (57) located proximal to the rear view module (51). The rear air/water channel (58) provides a jet of water and a stream of air that is used to clean the rear image lens (52) and the rear illumination bulb (53). It is also used to insufflate air in the field of vision of the rear image lens (52) for better distension and visualization. Surgical instruments are passed through the rear instrument channel (25) to do various surgical procedures in the area under view of the rear image lens (52). It is also used to direct suction to the area under the view of the rear image lens (52).

In the preferred embodiment, the rear air/water channel (58) and the rear instrument channel (59) is connected to the main air/water channel (24) and the main instrument channel (25) respectively. However, these may exist independently. Passage to the rear air/water channel (58) and rear instrument channel (59) from the main air/water channel (24) and main instrument channel (25) is controlled by a valve or any other suitable mechanical device. Typically, deployment of the rear view module (51) automatically opens the passage to the rear air/water channel (58) and the rear instrument channel (59). Alternatively, the passageways can be controlled independently.

Figure 22:
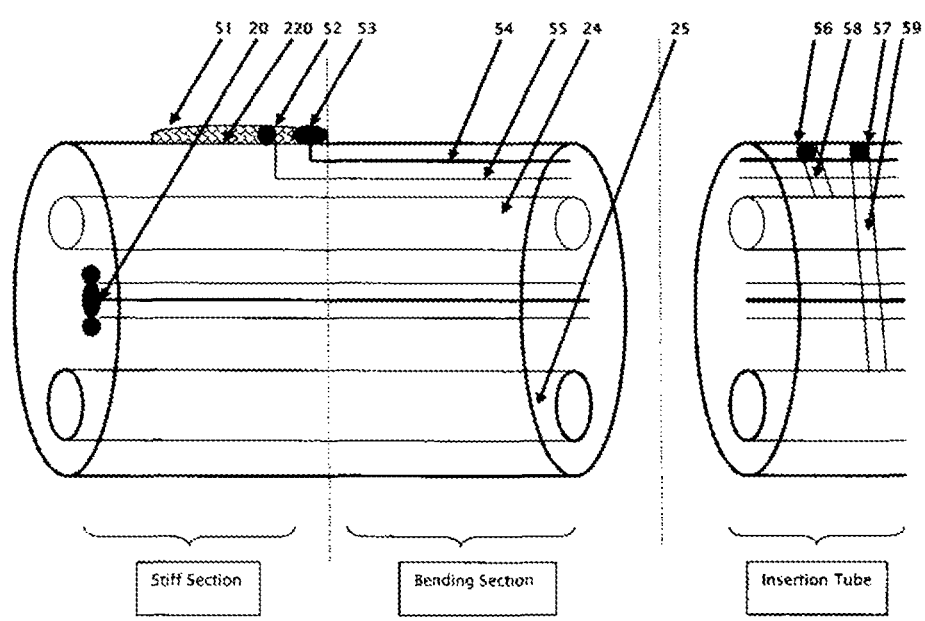
FIG. 22 shows side view of an endoscope with a 'rear view module' according to an eighth embodiment of the present invention.
Figure 23:
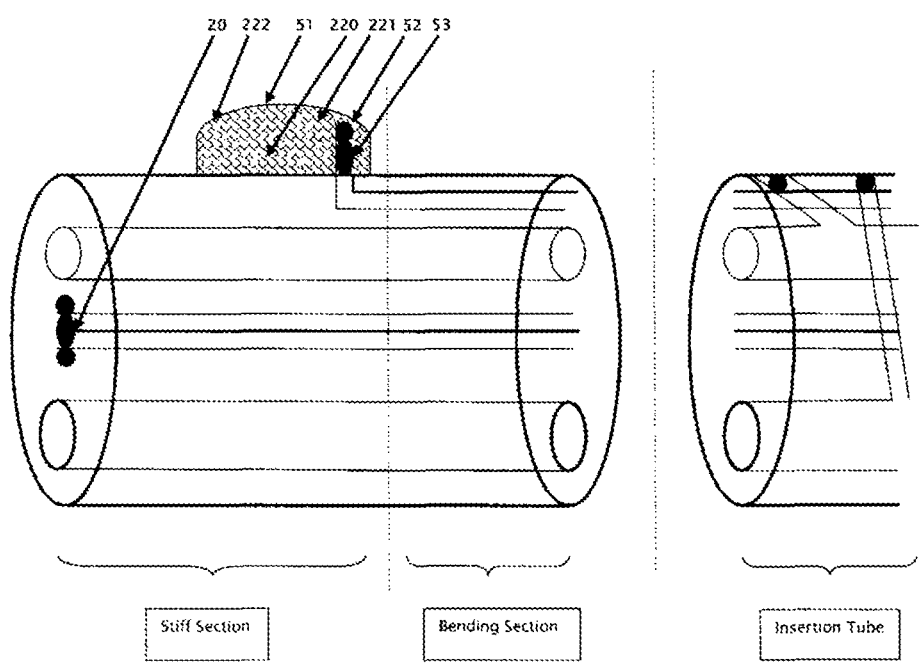
FIG. 23 is a side view of the endoscope in FIG. 22 wherein the 'rear view module' is deployed for rear view.

FIG. 22 shows side view of an eighth preferred embodiment of the present invention. The rear view module (51) consists of an inflatable balloon (220) or any other inflatable device that is attached to the stiff section of the endoscope. The balloon is connected to an air pump by a thin tube placed within the shaft of the endoscope (not shown). When inflated, the balloon (220) has a proximal face (221) and a distal face (222) as shown in FIG. 23. The proximal face (221) of the balloon contains the rear image lens (52) and the rear illumination bulb (53). Electric cables (54, 55) connect the rear image lens (52) to an image processor and the rear illumination bulb (53) to a power source.

In the preferred embodiment, there is a rear air/water channel (58) with a rear air/water nozzle (56) and rear instrument channel (59) with a rear instrument channel outlet (57) located proximal to the rear view module (51). The rear air/water channel (58) provides a jet of water and a stream of air that is used to clean the rear image lens (52) and the rear illumination bulb (53). It is also used to insufflate air in the field of vision of the rear image lens (52) for better distension and visualization. Surgical instruments are passed through the rear instrument channel (25) to do various surgical procedures in the area under view of the rear image lens (52). It is also used to direct suction to the area under the view of the rear image lens (52).

In the preferred embodiment, the rear air/water channel (58) and the rear instrument channel (59) is connected to the main air/water channel (24) and the main instrument channel (25) respectively. However, these may exist independently. Passage to the rear air/water channel (58) and rear instrument channel (59) from the main air/water channel (24) and main instrument channel (25) is controlled by a valve or any other suitable mechanical device. Typically, deployment of the rear view module (51) automatically opens the passage to the rear air/water channel (58) and the rear instrument channel (59). Alternatively, the passageways can be controlled independently.

Inflating the balloon (220) deploys the rear view module as shown in FIG. 23. When the balloon is fully inflated, the rear image lens (52) and the rear illumination bulb (53) face backwards. The rear image lens (52) gives a rear view and the rear illumination bulb (53) illuminates the area under view of the rear image lens (52). The main image lens (20) of the endoscope is able to give a forward view at the same time as the rear image lens (52) is giving a rear view. Hence, simultaneous forward and rear view is possible if the operator desires so.

In a variation to the present embodiment, there can be an additional forward image lens and an additional forward illumination bulb placed on the distal face (222) of the balloon. This will widen the forward field of vision when the balloon (220) is inflated.

Figure 24A:
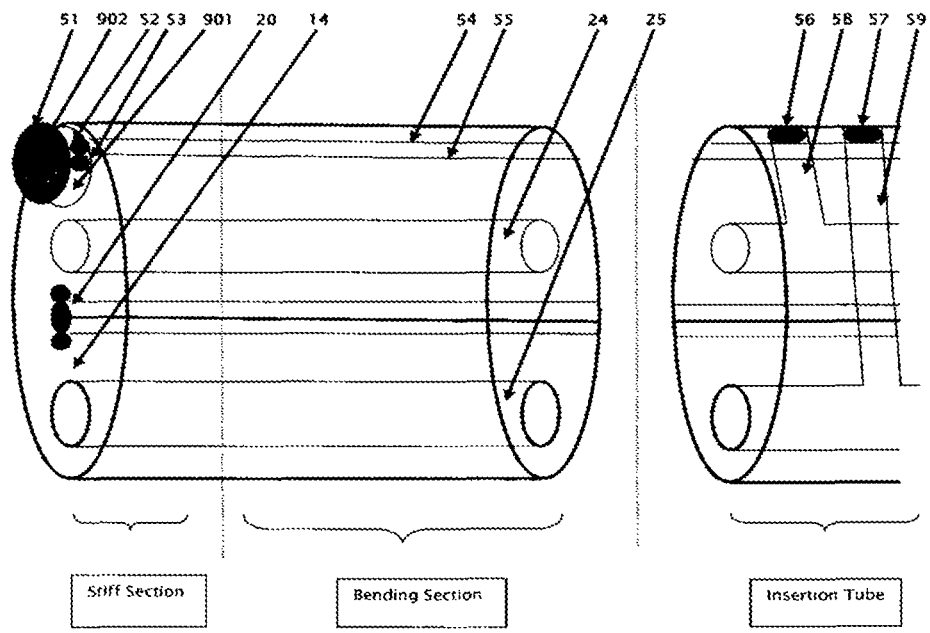
FIG. 24A shows side view of an endoscope with a 'rear view module' according to a ninth embodiment of the present invention.
Figure 24B:
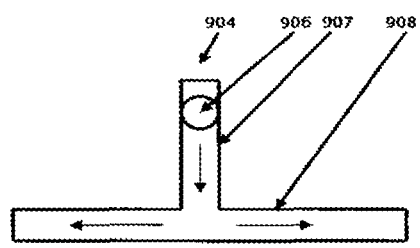
FIG. 24B shows a cross section view of an exemplary biplanar rolling joint that is used to attach a proximal face of the rear view module to the distal end of the endo scope in FIG. 24A.

FIG. 24A shows side view of a ninth preferred embodiment of the present invention. The rear view module (51) is a solid disc shaped structure that has a proximal face (901) and distal face (902). It is mounted on the distal end (14) of the endoscope. It comprises of a rear image lens (52) and a rear illumination bulb (53) that is placed on the proximal face (901). The rear image lens (52) is connected to an image processor and the rear illumination bulb (53) is connected to a power source by electrical cables (54, 55). In the preferred embodiment, the rear view module (51) is placed towards the periphery of the distal end (14) of the endoscope but it may be placed at anywhere on the distal end (14). The proximal face (901) of the rear view module is attached to the distal end (14) of the endoscope by a biplanar rolling joint (904) as shown in FIG. 24B. It allows rolling motion of the rear view module in both vertical and horizontal planes from the distal end (14). Alternatively, the rear view module may be attached using any other suitable mechanical articulation. As shown in FIG. 24B, a biplanar rolling joint (904) consists of two grooves (907,908) placed orthogonally to each other. A small wheel (906) is placed within the groove. The outer part of this wheel is movable and the inner part is fixed. The rear view module (51) is attached to the fixed inner part. The rear view module is moved by rotating the wheel (906) along the grooves (907, 908).

In the preferred embodiment, there is a rear air/water channel (58) with a rear air/water nozzle (56) and rear instrument channel (59) with a rear instrument channel outlet (57) located proximal to the rear view module (51). The rear air/water channel (58) provides a jet of water and a stream of air that is used to clean the rear image lens (52) and the rear illumination bulb (53). It is also used to insufflate air in the field of vision of the rear image lens (52) for better distension and visualization. Surgical instruments are passed through the rear instrument channel (25) to do various surgical procedures in the area under view of the rear image lens (52). It is also used to direct suction to the area under the view of the rear image lens (52).

In the preferred embodiment, the rear air/water channel (58) and the rear instrument channel (59) is connected to the main air/water channel (24) and the main instrument channel (25) respectively. However, these may exist independently. Passage to the rear air/water channel (58) and rear instrument channel (59) from the main air/water channel (24) and main instrument channel (25) is controlled by a valve or any other suitable mechanical device. Typically, deployment of the rear view module (51) automatically opens the passage to the rear air/water channel (58) and the rear instrument channel (59). Alternatively, the passageways can be controlled independently.

Figure 25:
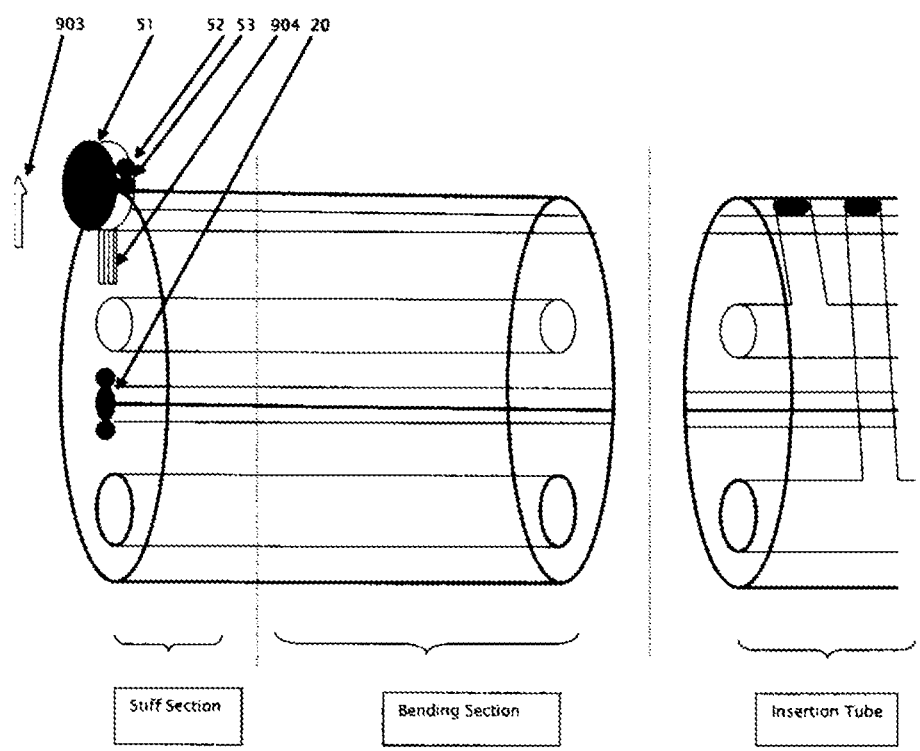
FIG. 25 is a side view of the endoscope in FIG. 24A wherein the 'rear view module' is deployed for rear view.

The rear view module (51) is deployed by rolling it vertically (903) from the distal end of the endoscope (14), as shown in FIG. 25. Alternatively the rear view module can be deployed by rolling it horizontally from the distal end (14). The extent of the roll is enough to move the rear image lens (52) and the rear illumination bulb (53) away from the distal end of the endoscope (14). In this position, the rear image lens (52) gives a rear view and the rear illumination bulb (53) illuminates the area under view of the rear image lens (52). The rear view module (51) can also be rotated to widen the rear field of view. This may cause some distortion of the image which can be corrected by modifying the software of the image processor. The main image lens (20) of the endoscope is able to give a forward view at the same time as the rear image lens (52) is giving a rear view. Hence, simultaneous forward and rear view is possible if so desired by the operator.

In a variation to the preferred embodiment the rear view module may contain an additional forward image lens and an additional forward illumination bulb on its distal face (902). This will widen the forward field of vision.

Figure 26:
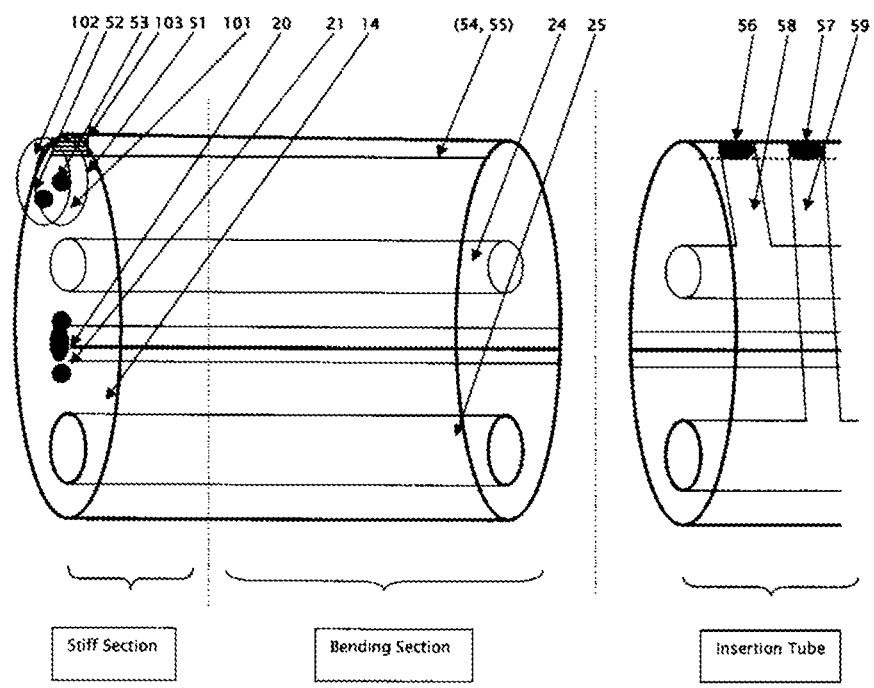
FIG. 26 shows side view of an endoscope with a 'rear view module' according to a tenth embodiment of the present invention.

FIG. 26 shows side view of a tenth preferred embodiment of the present invention. The rear view module (51) is a solid discoid structure that is mounted on the distal end of the endoscope (14). It has a proximal face (101) and a distal face (102). The rear view module (51) is attached to the distal end of the endoscope (14) by a hinge joint (103) or any other suitable mechanical articulation. The rear view module (51) has a rear image lens (52) and a rear illumination bulb (53) that is mounted on its distal face (102) of the module. The rear image lens (52) is connected to an image processor and the rear illumination bulb (53) is connected to a power source by electrical cables (54, 55). In resting position, the rear image lens (52) and the rear illumination bulb face forward and augment the main image lens (20) and the main illumination bulb (21) to widen the forward field of view. In the preferred embodiment, the rear view module (51) is placed at the periphery of the distal end of the endoscope (14) but it can be placed anywhere. The rear view module (51) is connected to a rear view module actuator by cables. Tension on these cables flips the rear view module (51) clockwise and anticlockwise vertically from the distal end of the endoscope (14). Alternatively, the rear view module can be flipped in a horizontal plane.

In the preferred embodiment, there is a rear air/water channel (58) with a rear air/water nozzle (56) and rear instrument channel (59) with a rear instrument channel outlet (57) located proximal to the rear view module (51). The rear air/water channel (58) provides a jet of water and a stream of air that is used to clean the rear image lens (52) and the rear illumination bulb (53). It is also used to insufflate air in the field of vision of the rear image lens (52) for better distension and visualization. Surgical instruments are passed through the rear instrument channel (25) to do various surgical procedures in the area under view of the rear image lens (52). It is also used to direct suction to the area under the view of the rear image lens (52).

In the preferred embodiment, the rear air/water channel (58) and the rear instrument channel (59) is connected to the main air/water channel (24) and the main instrument channel (25) respectively. However, these may exist independently. Passage to the rear air/water channel (58) and rear instrument channel (59) from the main air/water channel (24) and main instrument channel (25) is controlled by a valve or any other suitable mechanical device. Typically, deployment of the rear view module (51) automatically opens the passage to the rear air/water channel (58) and the rear instrument channel (59). Alternatively, the passageways can be controlled independently.

Figure 27:
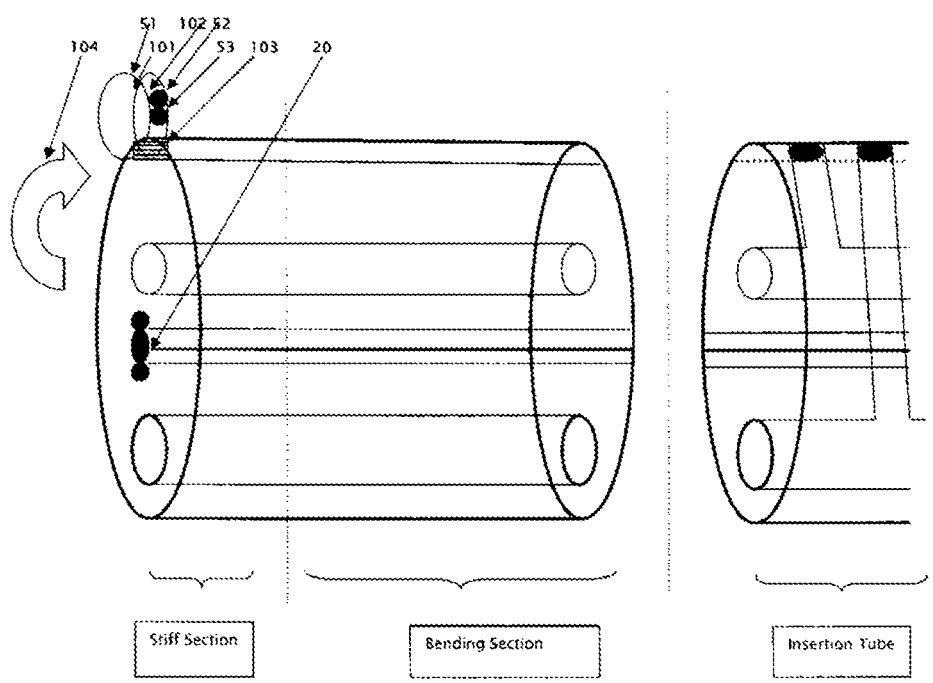
FIG. 27 is a side view of the endoscope in FIG. 26 wherein the 'rear view module' is deployed for rear view.

FIG. 27 shows the endoscope on FIG. 26 where the rear view module (51) has been deployed by flipping it vertically (104) from the distal end of the endoscope (14) to 180 degrees. In this position, the rear image lens (52) faces backward and gives a rear view. The rear illumination bulb (53) faces backward and illuminates the area under view of the rear image lens (52). The rear view module (51) can also be rotated in different directions to widen the rear field of vision. The main image lens (20) of the endoscope is able to give a forward view at the same time as the rear image lens (52) is giving a rear view. Hence, simultaneous forward and rear view is possible if the operator so desires.

In a variation to the preferred embodiment, the rear view module (51) may also contain an additional forward image lens and an additional forward illumination bulb on its proximal face (101). This will increase the forward field of vision when the rear view module is deployed (104) with its proximal face (101) facing forward.

Figure 28:
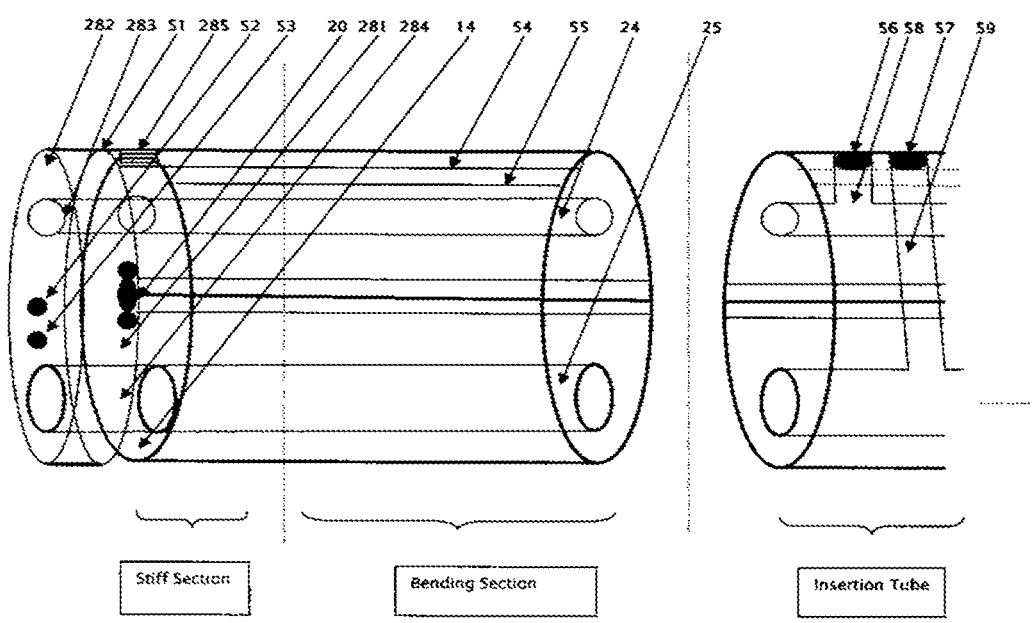
FIG. 28 shows side view of an endoscope with a 'rear view module' according to an eleventh embodiment of the present invention.
Figure 29:
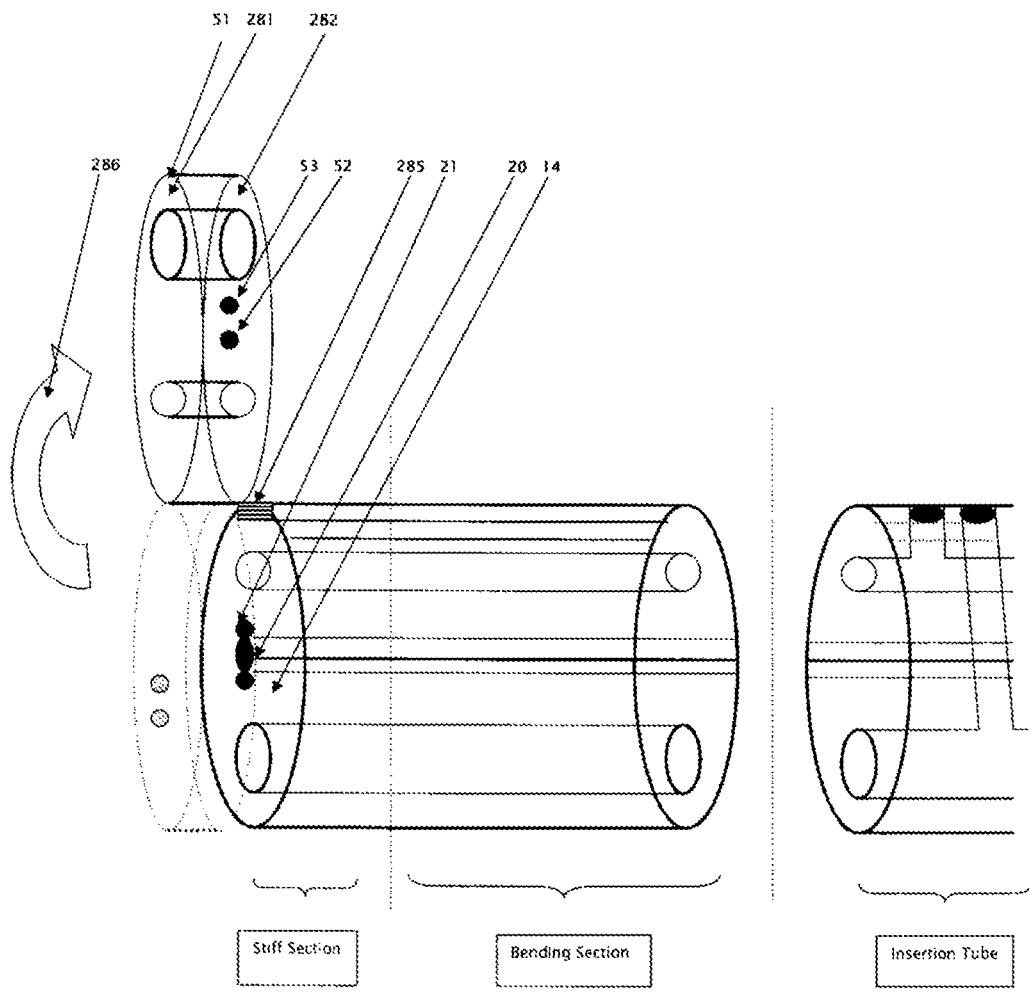
FIG. 29 is a side view of the endoscope in FIG. 28 wherein the 'rear view module' is deployed for rear view.

FIG. 28 shows side view of an eleventh preferred embodiment of the present invention. The rear view module (51) is a solid discoid structure that is placed in front of the distal end (14) of the endoscope. The periphery of the rear view module (51) is attached to the distal end (14) of the endoscope by a hinge joint (285) or any other suitable mechanical articulation. It has a proximal face (281) and a distal face (282). The rear image lens (52) and the rear illumination bulb (53) are placed on the distal face (282) of the rear view module. The rear image lens (52) is connected to an image processor and the rear illumination bulb (53) is connected to a power source by electric cables (54, 55). In resting position, the rear view module (51) covers the distal end of the endoscope (14) and faces forward. In this position, the rear image lens (52) gives a forward view and the rear illumination bulb (53) illuminates the area in front of the endoscope. In the preferred embodiment, the diameter of the rear view module (51) is the same as that of the distal end of the endoscope (14). The air/water channel (24) and the instrument channel (25) of the endoscope extend into the rear view module (283,284). The proximal and distal face of the rear view module (281, 282) is connected to a rear view module actuator by cables. Tension on these cables flips the rear view module (51) clockwise and anti clockwise vertically from the distal end of the endoscope (14) as shown in FIG. 29. Alternatively, the rear view module can be flipped horizontally.

In the preferred embodiment, there is a rear air/water channel (58) with a rear air/water nozzle (56) and rear instrument channel (59) with a rear instrument channel outlet (57) located proximal to the rear view module (51). The rear air/water channel (58) provides a jet of water and a stream of air that is used to clean the rear image lens (52) and the rear illumination bulb (53). It is also used to insufflate air in the field of vision of the rear image lens (52) for better distension and visualization. Surgical instruments are passed through the rear instrument channel (25) to do various surgical procedures in the area under view of the rear image lens (52). It is also used to direct suction to the area under the view of the rear image lens (52).

In the preferred embodiment, the rear air/water channel (58) and the rear instrument channel (59) is connected to the main air/water channel (24) and the main instrument channel (25) respectively. However, these may exist independently. Passage to the rear air/water channel (58) and rear instrument channel (59) from the main air/water channel (24) and main instrument channel (25) is controlled by a valve or any other suitable mechanical device. Typically, deployment of the rear view module (51) automatically opens the passage to the rear air/water channel (58) and the rear instrument channel (59). Alternatively, the passageways can be controlled independently.

FIG. 29 shows the endoscope in FIG. 28 where the rear view module (51) has been deployed by flipping it vertically from the distal end of the endoscope to 180 degrees (286) using the rear view module actuator. In this position, the rear image lens (52) and the rear illumination bulb (53) face backward. The rear image lens (52) gives a rear view and the rear illumination bulb (53) illuminates the area under view of the rear image lens (52). Further, the rear view module (51) can be rotated in this position to increase the rear field of view. Upon deployment, the rear view module (51) moves away from the front of the distal end (14) of the endoscope. It enables the main image lens (20) to give a forward view and the main illumination bulb (21) to illuminate the area in front of the distal end of the endoscope. This makes it possible to have simultaneous forward and rear view if so desired by the operator.

In a variation to the preferred embodiment, the rear view module contains an additional forward image lens and an additional forward illumination bulb on its proximal face (281). When the rear view module is deployed, the proximal face (281) with the additional forward image lens and additional illumination bulb faces forward and augments the main image lens (20) and the main illumination bulb (21. This widens the forward field of vision when the rear view module is deployed.

Figure 30:
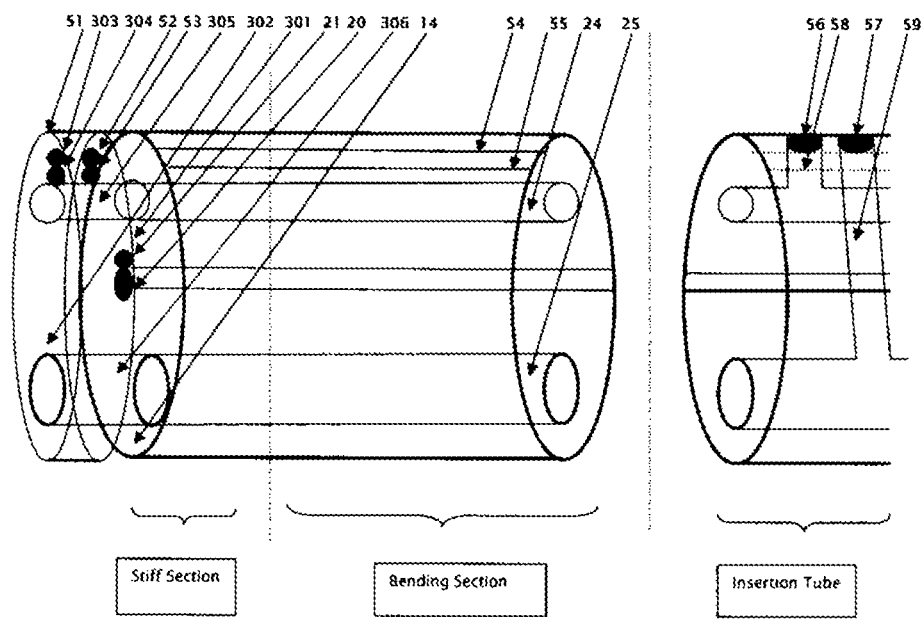
FIG. 30 shows side view of an endoscope with a 'rear view module' according to a twelfth embodiment of the present invention.

FIG. 30 shows side view of a twelfth preferred embodiment of the present invention. The rear view module (51) is a solid discoid structure that is placed in front of the distal end of the endoscope (14). It has a proximal face (301) and a distal face (302). The rear view module comprises of a rear image lens (52) connected to an image processor and a rear illumination bulb (53) connected to a power source by electric cables (54, 55). The rear image lens (52) and the rear illumination bulb (53) are placed on the proximal face (301) of the rear view module (51). In addition, the rear view module (51) has an additional image lens (303) and an additional illumination bulb (304) that is placed on its distal face (302). In the preferred embodiment, the diameter of the rear view module (51) is the same as that of the distal end of the endoscope (14). The main air/water channel (24) and the main instrument channel (25) of the endoscope extend into the rear view module (305, 306). The rear view module

(51) is attached to the distal end of the endoscope (14) by a biplanar rolling joint as shown in FIG. 24B. This allows rolling motion of the rear view module (51) both vertically and horizontally to the distal end of the endoscope (14). It may also be attached by any other suitable mechanical articulation. In resting position, the rear view module (51) covers the main image lens (20) and the main illumination bulb (21) of the endoscope. In this position, the additional image lens (303) and the additional illumination bulb (304) faces forward and gives a forward view and illuminates the area in front of the endoscope.

In the preferred embodiment, there is a rear air/water channel (58) with a rear air/water nozzle (56) and rear instrument channel (59) with a rear instrument channel outlet (57) located proximal to the rear view module (51). The rear air/water channel (58) provides a jet of water and a stream of air that is used to clean the rear image lens (52) and the rear illumination bulb (53). It is also used to insufflate air in the field of vision of the rear image lens (52) for better distension and visualization. Surgical instruments are passed through the rear instrument channel (25) to do various surgical procedures in the area under view of the rear image lens (52). It is also used to direct suction to the area under the view of the rear image lens (52).

In the preferred embodiment, the rear air/water channel (58) and the rear instrument channel (59) is connected to the main air/water channel (24) and the main instrument channel (25) respectively. However, these may exist independently. Passage to the rear air/water channel (58) and rear instrument channel (59) from the main air/water channel (24) and main instrument channel (25) is controlled by a valve or any other suitable mechanical device. Typically, deployment of the rear view module (51) automatically opens the passage to the rear air/water channel (58) and the rear instrument channel (59). Alternatively, the passageways can be controlled independently.

Figure 31:
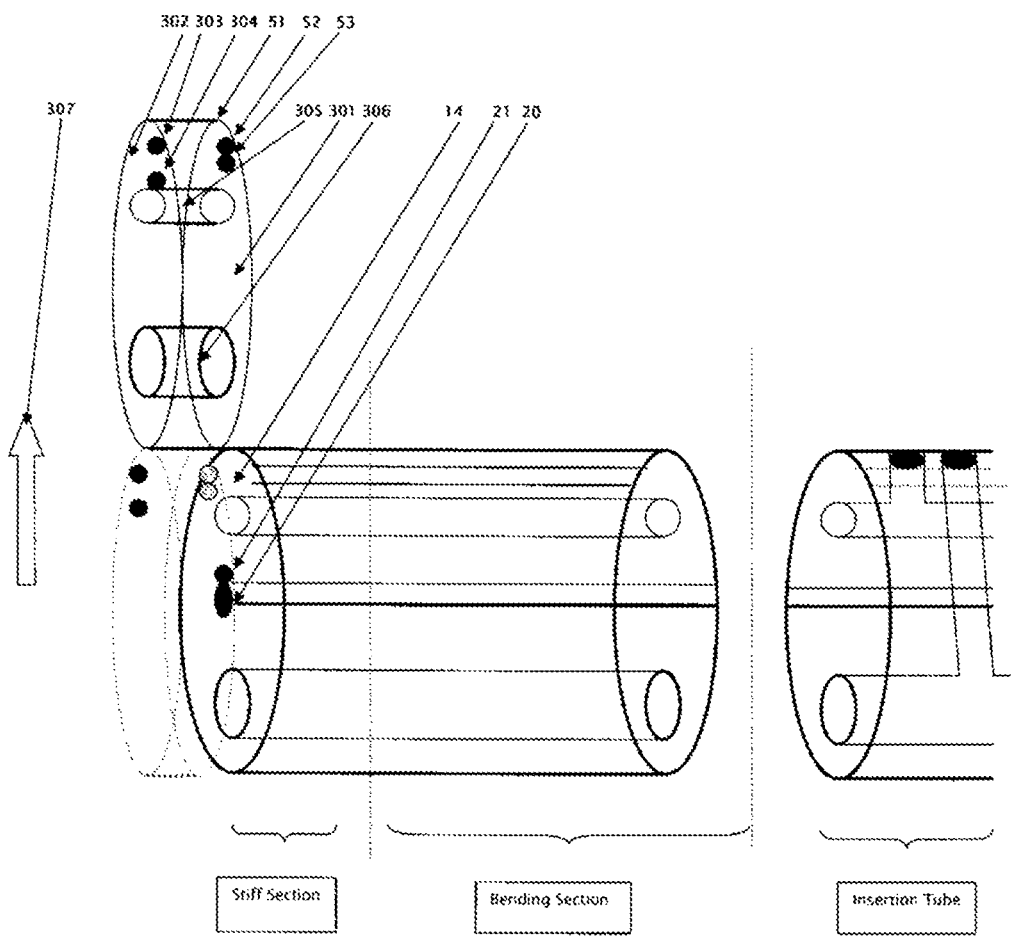
FIG. 31 is a side view of the endoscope in FIG. 30 wherein the 'rear view module' is deployed for rear view.

FIG. 31 shows the endoscope in the embodiment in FIG. 30 where the rear view module (51) has been deployed by sliding it vertically (307) from the distal end of the endoscope (14). Upon deployment, the rear image lens (52) and the rear illumination bulb (53) face backward. The rear image lens (52) gives a rear view and the rear illumination bulb (53) illuminates the area under view of the rear image lens (52). Further, the rear view module (51) can be rotated to increase the field of rear view. The rear view module (51) also moves away from front of the distal end of the endoscope (14) upon deployment. The main image lens (20) is then able to give a forward view and the main illumination bulb (21) is able to illuminate the area in front of the endoscope. Hence, the preferred embodiment provides simultaneous forward and rear view if so desired by the operator. The additional image lens (303) and the additional illumination bulb (304) augment the main image lens (20) and the main illumination bulb (21) and widen the forward field of vision when the rear view module (51) is deployed.

Any person/persons familiar with prior art will understand that modifications or changes to the present invention can be made without compromising its principles. In one variation of the present invention, the relative positions of the rear view module, rear air/water channel and the rear instrument channel may be changed. In another variation of the present invention, more than one rear view module, rear instrument channel and rear air/water channel can be present. According to another variation of the present invention, the rear view module, rear instrument channel and the rear air/water channel can be placed anywhere on the endoscope. According to yet another variation of the present invention, the shape, composition and configuration of the rear view module can be modified or changed without compromising the basic principles of the present invention. According to another variation of the present invention, the method of deployment of the rear view module can be modified without compromising the basic principles of the present invention. According to yet another variation of the present invention more than one rear image lens and/or more than one rear illumination bulb can be present. The above examples are only illustrative and by no means all inclusive.

What is claimed is:

1. An endoscope used to perform gastrointestinal endoscopy, the endoscope comprising:
   a shaft having a distal end receivable in a hollow gastrointestinal tract and a proximal end, the shaft extending from the distal end along a longitudinal axis towards the proximal end, the distal end and the proximal end defining a hollow channel extended therethrough, the hollow channel connected to and opening to one or more outlets on the distal end;
   a forward view module comprising a first lens positioned adjacent to the distal end of the shaft, the forward view module configured to have a forward field-of-vision when receiving a first image through the first lens while the distal end of the shaft is being received in the hollow gastrointestinal tract, the forward field-of-vision including a zero degree angle to the longitudinal axis in a forward direction pointing from the proximal end of the shaft to the distal end of the shaft; and
   a rearview module comprising a second lens, the rearview module disposed on the outer periphery of the shaft adjacent to the distal end of the shaft and configured to have a rearward field-of-vision when receiving a second image through the second lens when the distal end of the shaft is being received in the hollow gastrointestinal tract, the rearward field-of-vision including an acute angle to the longitudinal axis in a rearward direction pointing from the distal end of the shaft to the proximal end of the shaft; and
   a rearview air/water channel having a rearview air/water outlet, the rearview air/water outlet located on the outer periphery of the shaft and adjacent to the second lens, the rearview air/water channel configured to channel at least one of a water jet and an air stream out of the rearview air/water outlet in such a manner that the channeled at least one of the water jet and the air stream is directed to clean at least the second lens while the distal end of the shaft is being received in the hollow gastrointestinal tract and the forward view and rearview modules are being respectively configured to receive the first and second images;
   wherein the rearview module receives the second image substantially simultaneously with the forward view module receiving the first image;
   wherein one portion of the rearview air/water channel is situated and extended inside the hollow channel extended through the distal and proximal ends of the shaft;
   wherein the one or more outlets on the distal end of the shaft includes a main air/water outlet;
   wherein the endoscope further comprises a main air/water channel having the main air/water outlet, one portion of the main air/water channel situated and extended inside the hollow channel, the main air/water channel configured to channel, through the main air/water outlet, water or air into the hollow gastrointestinal tract; and wherein the one portion of the rearview air/water channel situated and extended inside the hollow channel is included within the one portion of the main air/water channel situated and extended inside the hollow channel.

2. The endoscope of claim 1, wherein the rearview module is configured to transition from having an initial field-of-vision during an undeployed state to having the rearward field-of-vision during a deployed state.

3. The endoscope of claim 1, wherein the rearview module is attached to the distal end of the shaft during an undeployed state before the rearview module is deployed to a deployed state during which the rearview module is configured to have the rearward field-of-vision, when the distal end of the shaft is being received in the hollow gastrointestinal tract.

4. The endoscope of claim 1, wherein the rearview module is disposed adjacent to the distal end of the shaft through an independent steering system when the distal end of the shaft is being received in the hollow gastrointestinal tract.

5. The endoscope of claim 1, wherein the rearview module is configured to transition from an undeployed state to a deployed state during which the rearview module is configured to have the rearward field-of-vision, through an actuating mechanism.

6. The endoscope of claim 1, further comprising:
a rearview instrument channel having a rearview instrument outlet located on the outer periphery of the shaft and adjacent to the rearview module, the rearview instrument channel configured to pass, through the rearview instrument outlet, instruments to do surgical procedures in an area within the rearward field-of-vision of the rearview module.

7. The endoscope of claim 6, wherein one portion of the rearview instrument channel is situated and extended inside the hollow channel extended through the distal end and the proximal end of the shaft.

8. The endoscope of claim 6, wherein the one or more outlets on the distal end of the shaft includes a main instrument outlet; and
wherein the endoscope further comprises a main instrument channel having the main instrument outlet, one portion of the main instrument channel situated and extended inside the hollow channel, the main instrument channel configured to pass, through the main instrument outlet, instruments to do surgical procedures in the hollow gastrointestinal tract.

9. The endoscope of claim 8, wherein the rearview instrument channel is extended inside the hollow channel independent of the main instrument channel.

10. The endoscope of claim 8, wherein the rearview instrument channel is connected to the main instrument channel.

* * * * *